US008871719B2

(12) United States Patent
Nakamura et al.

(10) Patent No.: US 8,871,719 B2
(45) Date of Patent: Oct. 28, 2014

(54) MODIFIED MELK PEPTIDES AND VACCINES CONTAINING THE SAME

(75) Inventors: Yusuke Nakamura, Tokyo (JP); Takuya Tsunoda, Kanagawa (JP); Ryuji Ohsawa, Kanagawa (JP); Sachiko Yoshimura, Kanagawa (JP); Tomohisa Watanabe, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 86 days.

(21) Appl. No.: 13/574,774

(22) PCT Filed: Jan. 24, 2011

(86) PCT No.: PCT/JP2011/000352
§ 371 (c)(1),
(2), (4) Date: Oct. 8, 2012

(87) PCT Pub. No.: WO2011/089921
PCT Pub. Date: Jul. 28, 2011

(65) Prior Publication Data
US 2013/0034574 A1 Feb. 7, 2013

Related U.S. Application Data

(60) Provisional application No. 61/297,996, filed on Jan. 25, 2010.

(51) Int. Cl.
*A61K 38/00* (2006.01)
*A61K 39/00* (2006.01)
*C12N 9/12* (2006.01)
*A61K 39/39* (2006.01)

(52) U.S. Cl.
CPC ..... *C12Y 207/11025* (2013.01); *A61K 39/0011* (2013.01); *A61K 39/39* (2013.01); *C12N 9/1205* (2013.01)
USPC ........... 514/19.2; 530/326; 530/327; 530/328

(58) Field of Classification Search
None
See application file for complete search history.

(56) References Cited

U.S. PATENT DOCUMENTS

| 6,229,001 | B1 | 5/2001 | Barrow et al. |
| 6,605,709 | B1 | 8/2003 | Breton |
| 6,833,447 | B1 | 12/2004 | Goldman et al. |
| 6,974,867 | B2 | 12/2005 | Wu et al. |
| 7,504,111 | B2 | 3/2009 | Fontana et al. |
| 7,504,120 | B2 | 3/2009 | Steer et al. |
| 7,998,695 | B2 | 8/2011 | Nakamura et al. |
| 8,067,671 | B2 | 11/2011 | Boukharov et al. |
| 2002/0049180 | A1 | 4/2002 | Wu et al. |
| 2002/0156263 | A1 | 10/2002 | Chen |
| 2008/0293044 | A1 | 11/2008 | Kadyk et al. |
| 2009/0175844 | A1 | 7/2009 | Nakamura et al. |
| 2009/0263395 | A1 | 10/2009 | Nakamura et al. |
| 2009/0317392 | A1 | 12/2009 | Nakamura et al. |
| 2011/0212115 | A1 | 9/2011 | Tsunoda et al. |
| 2012/0014996 | A1 | 1/2012 | Nakamura et al. |

FOREIGN PATENT DOCUMENTS

| CN | 101160524 A | 4/2008 |
| EP | 1930433 A1 | 6/2008 |
| JP | 2005-522999 A | 8/2005 |
| JP | 2008-509652 A | 4/2008 |
| KR | 1998/0026247 B1 | 7/1999 |
| WO | 03/065006 A2 | 8/2003 |
| WO | 2004/031413 A2 | 4/2004 |
| WO | 2004/070062 A2 | 8/2004 |
| WO | 2005/016279 A2 | 2/2005 |
| WO | 2005/039382 A2 | 5/2005 |
| WO | 2005/073374 * | 8/2005 |
| WO | 2005/073374 A1 | 8/2005 |
| WO | 2006/016525 A2 | 2/2006 |
| WO | 2006/085684 A2 | 8/2006 |
| WO | 2006/091734 A2 | 8/2006 |
| WO | 2007/013665 A2 | 2/2007 |
| WO | 2007/032255 A1 | 3/2007 |
| WO | 2008/023841 A1 | 2/2008 |
| WO | 2010/013485 A1 | 2/2010 |

OTHER PUBLICATIONS

Adams, et al., "Prediction of binding to MHC class I molecules," *J Immunol Methods*, vol. 185(2), pp. 181-190 (Sep. 25, 1995).
Bachinsky, et al., "Mapping and binding analysis of peptides derived from the tumor-associated antigen survivin for eight HLA alleles," *Cancer Immun.*, vol. 5, 9 pages (Mar. 22, 2005).
Baker, et al., "Suppression of Human Colorectal Carcinoma Cell Growth by Wild-Type p53," *Science*, vol. 249(4971), pp. 912-915 (Aug. 24, 1990).
Belli, et al., "Vaccination of Metastatic Melanoma Patients With Autologous Tumor-Derived Heat Shock Protein gp96-Peptide Complexes: Clinical and Immunologic Findings," *J Clin Oncol.*, vol. 20(20), pp. 4169-4180 (Oct. 15, 2002).

(Continued)

*Primary Examiner* — Sheela J Huff
(74) *Attorney, Agent, or Firm* — Kilpatrick Townsend & Stockton LLP

(57) ABSTRACT

Isolated peptides composed of the amino acid sequence of the modified MELK epitope peptide or immunologically active fragments thereof that bind to HLA antigens and have higher cytotoxic T lymphocyte (CTL) inducibility than that of the wild type MELK epitope peptide and thus are suitable for use in the context of cancer immunotherapy or endometriosis immunotherapy, more particularly cancer or endometriosis vaccines are described herein. The present invention further provides peptides that include one, two, or several amino acid insertions, substitutions or additions to the aforementioned peptides or fragments, but yet retain the requisite cytotoxic T cell inducibility. Further provided are nucleic acids encoding any of these aforementioned peptides as well as pharmaceutical substances and compositions including any of the aforementioned peptides or nucleic acids. The peptides, nucleic acids, pharmaceutical substances and compositions of this invention find particular utility in the treatment of cancers, tumors, and endometriosis.

14 Claims, 9 Drawing Sheets

(56) References Cited

OTHER PUBLICATIONS

Blot, et al., "Cell Cycle Regulation of pEg3, a New *Xenopus* Protein Kinase of the KIN1/PAR-1/MARK Family," *Dev Biol.*, vol. 241(2), pp. 327-338 (Jan. 15, 2002).

Boon, "Tumor Antigens Recognized by Cytolytic T Lymphocytes: Present Perspectives for Specific Immunotherapy," *Int J Cancer*, vol. 54(2), pp. 177-180 (May 8, 1993).

Boon, et al., "Human Tumor Antigens Recognized by T Lymphocytes," *J Exp Med.*, vol. 183(3), pp. 725-729 (Mar. 1, 1996).

Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).

Coulie, et al., "Cytolytic T-cell responses of cancer patients vaccinated with a MAGE antigen," *Immunol Rev.*, vol. 188, pp. 33-42 (Oct. 2002).

Davezac, et al., "Human pEg3 kinase associates with and phosphorylates CDC25B phosphatase: a potential role for pEg3 in cell cycle regulation," *Oncogene*, vol. 21(50), pp. 7630-7641 (Oct. 31, 2002).

Drewes, et al., "The protein kinase kin1, the fission yeast orthologue of mammalian MARK/PAR-1, localises to new cell ends after mitosis and is important for bipolar growth," *Febs Lett*, vol. 554(1-2), pp. 45-49 (Nov. 6, 2003).

Fujie, et al., A *Mage*-1-Encoded HLA-A24 0Binding Synthetic Peptide Induces Specific Anti-Tumor Cytotoxic T Lymphocytes, *Int J Cancer*, vol. 80(2), pp. 169-72 (Jan. 18, 1999).

Gray, et al., "Maternal Embryonic Leucine Zipper Kinase/Murine Protein Serine-Threonine Kinase 38 is a Promising Therapeutic Target for Multiple Cancers," *Cancer Res.*, vol. 65(21), pp. 9751-9761 (Nov. 1, 2005).

Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).

Heyer, et al., "Expression of *Melk*, a New Protein Kinase, During Early Mouse Development," *Dev Dyn.*, vol. 215(4), pp. 344-351 (Aug. 1999).

Kikuchi, et al., "Identification of a Sart-1-Derived Peptide Capable of Inducing HLA-A24-Restricted and Tumor-Specific Cytotoxic T Lymphocytes," *Int J Cancer.*, vol. 81(3), pp. 459-466 (May 5, 1999).

Kuzushima, et al., "Efficient identification of HLA-A *2402-restricted cytomegalovirus-specific CD8+ T-cell epitopes by a computer algorithm and an enzyme-linked immunospot assay," *Blood.*, vol. 98(6), pp. 1872-1881 (Sep. 15, 2001).

Lin, et al., "Characterization of novel molecular targets for development of anti-cancer drugs for human breast cancer," *Nihonganqakkai Shouroku*, vol. 63, p. 75, W-116 (2004).

Lin., et al., "MMK4 is a promising therapeutic target for breast cancer," *The American Association for Cancer Research/AACR*, vol. 47; pp. 1134, #4829 (2006).

Lin, et al., "Involvement of maternal embryonic leucine zipper kinase (MELK) in mammary carcinogenesis through interaction with Bcl-G, a pro-apoptotic member for the Bcl-2 family," *Breast Cancer Res.*, vol. 9 (1), R17, 13 pages (2007).

Meng, et al., "Characterization of MMK4 as a novel molecular target for development of anti-cancer drugs for human breast cancer," *Nihongangakkai Shouroku*, vol. 65, p. 155, p. 231 (2006).

Morgan, et al., "High Efficiency TCR Gene Transfer into Primary Human Lymphocytes Affords Avid Recognition of Melanoma Tumor Antigen Glycoprotein 100 and Does Not Alter the Recognition of Autologous Melanoma Antigens," *J Immunol.*, vol. 171(6), pp. 3287-3295 (Sep. 15, 2003).

Nakano, et al., "Molecular characterization of maternal leucine-zipper kinase (MELK) in central nervous system stem/progenitor cells," *Planner*, 124.4, 1 page (2003).

Nakano, et al., "Maternal embryonic leucine zipper kinase (MELK) regulates multipotent neural progenitor proliferation," *J Cell Biol.*, vol. 170(3), pp. 413-427 (Aug. 1, 2005).

Oiso, et al., "A Newly Identified *Mage*-3-Derived Epitope Recognized by HLA-A24-Restricted Cytotoxic T Lymphocytes," *Int J Cancer*, vol. 81(3), pp. 387-394 (May 5, 1999).

Parker, et al., "Scheme for Ranking Potential HLA-A2 Binding Peptides Based on Independent Binding of Individual Peptide Side-Chains," *J Immunol.*, vol. 152(1), pp. 163-175 (Jan. 1, 1994).

Rosenberg, et al., "Cancer Immunotherapy: moving beyond current vaccines," *Nat Med.*, vol. 10(9), pp. 909-915 (Sep. 2004).

Salazar, et al., "Agonist Peptide From a Cytotoxic T-Lymphocyte Epitope of Human Carcinoembryonic Antigen Stimulates Production of Tc1-Type Cytokines and Increases Tyrosine Phosphorylation More Efficiently Than Cognate Peptide," *Int J Cancer.*, vol. 85(6), pp. 829-838 (Mar. 15, 2000).

Seong, et al., "Phosphorylation of a novel zinc-finger-like protein, ZPR9, by murine protein serine/threonine kinase 38 (MPK38)," *Biochem J.*, vol. 361(Pt 3), pp. 597-604 (Feb. 1, 2002).

Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).

Tassan, et al., "An overview of the KIN1/PAR-1/MARK kinase family," *Biol Cell.*, vol. 96(3), pp. 193-199 (Apr. 2004).

Valmori, et al., "Enhanced Generation of Specific Tumor-Reactive CTL In Vitro by Selected Melan-A/MART-1 Immunodominant Peptide Analogues," *J Immunol.*, vol. 160(4), pp. 1750-1758 (Feb. 15, 1998).

Van Der Burg, et al., "Immunogenicity of Peptides Bound to MHC Class I Molecules Depends on the MHC-Peptide Complex Stability," *J Immunol.*, vol. 156(9), pp. 3308-3314 (May 1, 1996).

Vissers, et al., "The Renal Cell Carcinoma-associated Antigen G250 Encodes a Human Leukocyte Antigen (HLA)-A2.1-restricted Epitope Recognized by Cytotoxic T Lyrnphocytes," *Cancer Res.*, vol. 59(21), pp. 5554-5559 (Nov. 1, 1999).

Vulsteke, et al., "Inhibition of Spliceosome Assmbly by the Cell Cycle-regulated Protein Kinase MELK and Involvement of Splicing Factor NIPP1," *J Biol Chem.*, vol. 279(10), pp. 8642-8647 (Mar. 5, 2004, Epub Dec. 29, 2003).

Database Geneseq, ABB04768, 1 page, dated Mar. 13, 2002.
Database Geneseq, ADE38347, 1 page, dated Jan. 29, 2004.
U.S. Appl. No. 11/573,394, downloaded May 31, 2011, 12 pages.
U.S. Appl. No. 13/056,598, 47 pages, filed May 23, 2011.
U.S. Appl. No. 13/536,327, 204 pages, filed Jun. 28, 2012.
International Search Report for PCT/JP2011/000352, mailed Feb. 15, 2011, 1 page.

Dionne, et al., "Functional characterization of CTL against gp100 altered peptide ligands," *Cancer Immunol Immunother.*, vol. 52(4), pp. 199-206 (Apr. 2003, Epub Feb. 18, 2003).

Dionne, et al., "Her-2/*neu* altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).

Falk, et al., "Allele-specific motifs revealed by sequencing of self-peptides eluted from MHC molecules," *Nature*, vol. 351(6324), pp. 290-296 (May 23, 1991).

Hoffmann, et al., "The Ability of Variant Peptides to Reverse the Nonresponsiveness of T Lymphocytes to the Wild-Type Sequence P53$_{264-272}$ Epitope," *J Immunol.*, vol. 168(3), pp. 1338-1347 (Feb. 1, 2002).

Kondo, et al., "Prominent Roles of Secondary Anchor Residues in Peptide Binding to HLA-A24 Human Class I Molecules," *J Immunol.*, vol. 155(9), pp. 4307-4312 (Nov. 1, 1995).

Kubo, et al., "Definition of Specific Peptide Motifs for Four Major HLA-A Alleles," *J Immunol.*, vol. 152(8), pp. 3913-3924 (Apr. 15, 1994).

Rammensee, et al., "MHC ligands and peptide motifs: first listing," *Immunogenetics*, vol. 41(4), pp. 178-228 (1995).

Schueler-Furman, et al., "Structure-based prediction of binding peptides to MHC class I molecules: Application to a broad range of MHC alleles," *Protein Sci.*, vol. 9(9), pp. 1838-1846 (Sep. 2000).

Zaremba, et al., "Identification of an Enhancer Agonist Cytotoxic T Lymphocytes Peptide from Human Carcinoembryonic Antigen," *Cancer Res.*, vol. 57(20), pp. 4570-4577 (Oct. 15, 1997).

Gil, et al., "Cloning and expression of a cDNA encoding a novel protein serine/threonine kinase predominately expressed in hematopoietic cells," *Gene*, vol. 195(2), pp. 295-301 (Aug. 22, 1997).

(56) References Cited

OTHER PUBLICATIONS

Gil, et al., "MPK38 expression is upregulated in immature T cells activated by concanavalin A," *Immunol Lett.*, vol. 64(2-3), pp. 79-83 (Dec. 1998).

U.S. Appl. No. 14/171,532, filed Feb. 3, 2014, 48 pages.

Dermer, "Another Anniversary for the War on Cancer," *Bio/Technology*, vol. 12, pp. 320 (1994).

Engelhard, "Structure of peptides associated with MHC class I molecules," *Curr Opin Immunol.*, vol. 6(1), pp. 13-23 (Feb. 1994).

Ezzell, "Cancer "Vaccines": An Idea Whose Time Has Come?," *J NIH Res.*, vol. 7, p. 46 (1995).

Freshney, et al., Culture of Animal Cells, A Manual of Basic Technique, pp. 3-4 (1983).

Graham, et al., "A novel strategy for the identification of antigens that are recognized by bovine MHC class I restricted cytotoxic T cells in a protozoan infection using reverse vaccinology," *Immunome Res.*, vol. 3(2), 9 pages, (Feb. 9, 2007).

Guo, et al., "Different length peptides bind to HLA-Aw68 similarly at their ends but bulge out in the middle," *Nature*, vol. 360(6402), pp. 364-366 (Nov. 26, 1992).

Gura, "Systems for Identifying New Drugs are Often Faulty," *Science*, vol. 278(5340), pp. 1041-1042 (Nov. 7, 1997).

Jain, "Barriers to Drug Delivery in Solid Tumors," *Sci Am.*, vol. 271(1), pp. 58-65 (Jul. 1994).

Johnson, et al., "The clinical impact of screening and other experimental tumor studies," *Cancer Treat Rev.*, vol. 2(1), pp. 1-31 (Mar. 1975).

Sasada, et al., "Identification of HLA-A*0201-restricted cytotoxic T lymphocyte (CTL) epitopes from a novel melanoma antigen, maternal embryonic leucine zipper kinase (MELK)," *Proceedings of the American Association for Cancer Research Annual Meeting*, 1001-2, vol. 49, 99th AACR Annual Meeting, Apr. 12-16, 2008.

Shastri, et al., "Presentation of Endogenous Peptide/MHC Class I Complexes is Profoundly Influenced by Specific C-Terminal Flanking Residues," *J Immunol.*, vol. 155(9), pp. 4339-4346 (Nov. 1, 1995).

Spitler, "Cancer Vaccines: The Interferon Analogy," *Cancer Biother.*, vol. 10(1), pp. 1-3 (Spring 1995).

Wada, et al., "Rationale for Antiangiogenic Cancer Therapy with Vaccination Using Epitope Peptides Derived from Human Vascular Endothelial Growth Factor Receptor 2," *Cancer Res.*, vol. 65(11), pp. 4939-4946 (Jun. 1, 2005).

Zhou, et al., "Screening and Identification of Severe Acute Respiratory Syndrome-Associated Coronavirus-Specific CTL Epitopes," *J Immunol.*, vol. 177(4), pp. 2138-2145 (Aug. 15, 2006).

\* cited by examiner

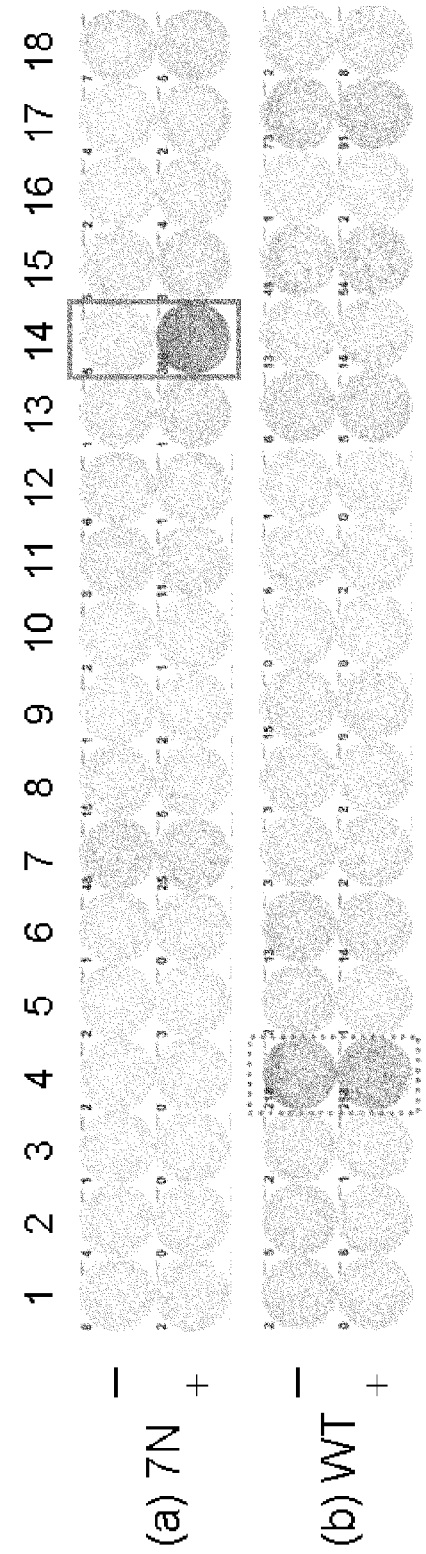

Establishment of CTL lines

Donor B

Donor C

Establishment of CTL clones

Donor B

Donor C a MELK-A24-9-199 clone b MELK-A24-9-199 clone the

SEQUENCE LISTING

```
<160> NUMBER OF SEQ ID NOS: 52

<210> SEQ ID NO 1
<211> LENGTH: 9
<212> TYPE: PRT
<213> ORGANISM: Artificial
<220> FEATURE:
<223> OTHER INFORMATION: An artificially synthesized peptide

<400> SEQUENCE: 1

Leu Tyr Val Leu Met Cys Gly Phe Leu
1               5

<210> SEQ ID NO 2
<211> LENGTH: 9
<212> TYPE: PRT
<213> ORGANISM: Artificial
<220> FEATURE:
<223> OTHER INFORMATION: An artificially synthesized peptide

<400> SEQUENCE: 2

Asp Tyr Ile Ile Ser Gln Asp Arg Leu
1               5
```

```
<210> SEQ ID NO 3
<211> LENGTH: 9
<212> TYPE: PRT
<213> ORGANISM: Artificial
<220> FEATURE:
<223> OTHER INFORMATION: An artificially synthesized peptide

<400> SEQUENCE: 3

His Tyr Asn Val Thr Thr Thr Arg Leu
1               5

<210> SEQ ID NO 4
<211> LENGTH: 9
<212> TYPE: PRT
<213> ORGANISM: Artificial
<220> FEATURE:
<223> OTHER INFORMATION: An artificially synthesized peptide

<400> SEQUENCE: 4

Asp Tyr Asp Trp Cys Glu Asp Asp Leu
1               5

<210> SEQ ID NO 5
<211> LENGTH: 9
<212> TYPE: PRT
<213> ORGANISM: Artificial
<220> FEATURE:
<223> OTHER INFORMATION: An artificially synthesized peptide

<400> SEQUENCE: 5

Lys Tyr Tyr Glu Leu His Glu Thr Ile
1               5

<210> SEQ ID NO 6
<211> LENGTH: 9
<212> TYPE: PRT
<213> ORGANISM: Artificial
<220> FEATURE:
<223> OTHER INFORMATION: An artificially synthesized peptide

<400> SEQUENCE: 6

Glu Tyr Cys Pro Gly Gly Glu Leu Phe
1               5

<210> SEQ ID NO 7
<211> LENGTH: 9
<212> TYPE: PRT
<213> ORGANISM: Artificial
<220> FEATURE:
<223> OTHER INFORMATION: An artificially synthesized peptide

<400> SEQUENCE: 7

Val Tyr Lys Arg Leu Val Glu Asp Ile
1               5

<210> SEQ ID NO 8
<211> LENGTH: 9
<212> TYPE: PRT
<213> ORGANISM: Artificial
<220> FEATURE:
<223> OTHER INFORMATION: An artificially synthesized peptide

<400> SEQUENCE: 8

Gln Phe Glu Leu Glu Val Cys Gln Leu
1               5

<210> SEQ ID NO 9
```

```
<211> LENGTH: 9
<212> TYPE: PRT
<213> ORGANISM: Artificial
<220> FEATURE:
<223> OTHER INFORMATION: An artificially synthesized peptide

<400> SEQUENCE: 9

Asp Phe Val Gln Lys Gly Tyr Thr Leu
1               5

<210> SEQ ID NO 10
<211> LENGTH: 9
<212> TYPE: PRT
<213> ORGANISM: Artificial
<220> FEATURE:
<223> OTHER INFORMATION: An artificially synthesized peptide

<400> SEQUENCE: 10

Val Phe Gly Ser Leu Glu Arg Gly Leu
1               5

<210> SEQ ID NO 11
<211> LENGTH: 9
<212> TYPE: PRT
<213> ORGANISM: Artificial
<220> FEATURE:
<223> OTHER INFORMATION: An artificially synthesized peptide

<400> SEQUENCE: 11

Arg Leu Val Asn Pro Asp Gln Leu Leu
1               5

<210> SEQ ID NO 12
<211> LENGTH: 9
<212> TYPE: PRT
<213> ORGANISM: Artificial
<220> FEATURE:
<223> OTHER INFORMATION: An artificially synthesized peptide

<400> SEQUENCE: 12

Asp Phe Gly Lys Val Thr Met Gln Phe
1               5

<210> SEQ ID NO 13
<211> LENGTH: 9
<212> TYPE: PRT
<213> ORGANISM: Artificial
<220> FEATURE:
<223> OTHER INFORMATION: An artificially synthesized peptide

<400> SEQUENCE: 13

Lys Gly Ala Lys Val Phe Gly Ser Leu
1               5

<210> SEQ ID NO 14
<211> LENGTH: 9
<212> TYPE: PRT
<213> ORGANISM: Artificial
<220> FEATURE:
<223> OTHER INFORMATION: An artificially synthesized peptide

<400> SEQUENCE: 14

Arg Gly Lys Pro Val Arg Leu Arg Leu
1               5

<210> SEQ ID NO 15
<211> LENGTH: 9
```

```
<212> TYPE: PRT
<213> ORGANISM: Artificial
<220> FEATURE:
<223> OTHER INFORMATION: An artificially synthesized peptide

<400> SEQUENCE: 15

Lys Asn Gln His Lys Arg Glu Ile Leu
1               5

<210> SEQ ID NO 16
<211> LENGTH: 9
<212> TYPE: PRT
<213> ORGANISM: Artificial
<220> FEATURE:
<223> OTHER INFORMATION: An artificially synthesized peptide

<400> SEQUENCE: 16

Lys Trp Leu Ser Pro Ser Ser Ile Leu
1               5

<210> SEQ ID NO 17
<211> LENGTH: 9
<212> TYPE: PRT
<213> ORGANISM: Artificial
<220> FEATURE:
<223> OTHER INFORMATION: An artificially synthesized peptide

<400> SEQUENCE: 17

Lys Tyr Trp Thr Glu Ser Asn Gly Val
1               5

<210> SEQ ID NO 18
<211> LENGTH: 9
<212> TYPE: PRT
<213> ORGANISM: Artificial
<220> FEATURE:
<223> OTHER INFORMATION: An artificially synthesized peptide

<400> SEQUENCE: 18

Arg Cys Arg Ser Val Glu Leu Asp Leu
1               5

<210> SEQ ID NO 19
<211> LENGTH: 9
<212> TYPE: PRT
<213> ORGANISM: Artificial
<220> FEATURE:
<223> OTHER INFORMATION: An artificially synthesized peptide

<400> SEQUENCE: 19

Lys Leu Lys Leu Ile Asp Phe Gly Leu
1               5

<210> SEQ ID NO 20
<211> LENGTH: 9
<212> TYPE: PRT
<213> ORGANISM: Artificial
<220> FEATURE:
<223> OTHER INFORMATION: An artificially synthesized peptide

<400> SEQUENCE: 20

Leu Leu Asn Glu Ile Met Ser Ile Leu
1               5

<210> SEQ ID NO 21
<211> LENGTH: 9
<212> TYPE: PRT
```

```
<213> ORGANISM: Artificial
<220> FEATURE:
<223> OTHER INFORMATION: An artificially synthesized peptide

<400> SEQUENCE: 21

Thr Ala Asn Lys Ile Phe Met Val Leu
1               5

<210> SEQ ID NO 22
<211> LENGTH: 9
<212> TYPE: PRT
<213> ORGANISM: Artificial
<220> FEATURE:
<223> OTHER INFORMATION: An artificially synthesized peptide

<400> SEQUENCE: 22

Lys Tyr Asp Val Pro Lys Trp Leu Ser
1               5

<210> SEQ ID NO 23
<211> LENGTH: 10
<212> TYPE: PRT
<213> ORGANISM: Artificial
<220> FEATURE:
<223> OTHER INFORMATION: An artificially synthesized peptide

<400> SEQUENCE: 23

Val Tyr Lys Arg Leu Val Glu Asp Ile Leu
1               5                   10

<210> SEQ ID NO 24
<211> LENGTH: 10
<212> TYPE: PRT
<213> ORGANISM: Artificial
<220> FEATURE:
<223> OTHER INFORMATION: An artificially synthesized peptide

<400> SEQUENCE: 24

Gln Tyr Asp His Leu Thr Ala Thr Tyr Leu
1               5                   10

<210> SEQ ID NO 25
<211> LENGTH: 10
<212> TYPE: PRT
<213> ORGANISM: Artificial
<220> FEATURE:
<223> OTHER INFORMATION: An artificially synthesized peptide

<400> SEQUENCE: 25

Glu Tyr His Lys Leu Lys Leu Ile Asp Phe
1               5                   10

<210> SEQ ID NO 26
<211> LENGTH: 10
<212> TYPE: PRT
<213> ORGANISM: Artificial
<220> FEATURE:
<223> OTHER INFORMATION: An artificially synthesized peptide

<400> SEQUENCE: 26

Leu Phe Asp Glu Tyr His Lys Leu Lys Leu
1               5                   10

<210> SEQ ID NO 27
<211> LENGTH: 10
<212> TYPE: PRT
<213> ORGANISM: Artificial
```

```
<220> FEATURE:
<223> OTHER INFORMATION: An artificially synthesized peptide

<400> SEQUENCE: 27

Arg Gly Leu Asp Lys Val Ile Thr Val Leu
1               5                   10

<210> SEQ ID NO 28
<211> LENGTH: 10
<212> TYPE: PRT
<213> ORGANISM: Artificial
<220> FEATURE:
<223> OTHER INFORMATION: An artificially synthesized peptide

<400> SEQUENCE: 28

Lys Trp Leu Ser Pro Ser Ser Ile Leu Leu
1               5                   10

<210> SEQ ID NO 29
<211> LENGTH: 10
<212> TYPE: PRT
<213> ORGANISM: Artificial
<220> FEATURE:
<223> OTHER INFORMATION: An artificially synthesized peptide

<400> SEQUENCE: 29

Lys Thr Glu Ile Glu Ala Leu Lys Asn Leu
1               5                   10

<210> SEQ ID NO 30
<211> LENGTH: 10
<212> TYPE: PRT
<213> ORGANISM: Artificial
<220> FEATURE:
<223> OTHER INFORMATION: An artificially synthesized peptide

<400> SEQUENCE: 30

Arg Asn Asn Arg Gln Thr Met Glu Asp Leu
1               5                   10

<210> SEQ ID NO 31
<211> LENGTH: 10
<212> TYPE: PRT
<213> ORGANISM: Artificial
<220> FEATURE:
<223> OTHER INFORMATION: An artificially synthesized peptide

<400> SEQUENCE: 31

Arg Gly Lys Tyr Asp Val Pro Lys Trp Leu
1               5                   10

<210> SEQ ID NO 32
<211> LENGTH: 10
<212> TYPE: PRT
<213> ORGANISM: Artificial
<220> FEATURE:
<223> OTHER INFORMATION: An artificially synthesized peptide

<400> SEQUENCE: 32

Lys Gly Asp Ala Trp Val Tyr Lys Arg Leu
1               5                   10

<210> SEQ ID NO 33
<211> LENGTH: 10
<212> TYPE: PRT
<213> ORGANISM: Artificial
<220> FEATURE:
```

<223> OTHER INFORMATION: An artificially synthesized peptide

<400> SEQUENCE: 33

Asp Tyr Asn Tyr Pro Val Glu Trp Gln Ser
1               5                   10

<210> SEQ ID NO 34
<211> LENGTH: 10
<212> TYPE: PRT
<213> ORGANISM: Artificial
<220> FEATURE:
<223> OTHER INFORMATION: An artificially synthesized peptide

<400> SEQUENCE: 34

Arg Tyr Thr Thr Pro Ser Lys Ala Arg Asn
1               5                   10

<210> SEQ ID NO 35
<211> LENGTH: 9
<212> TYPE: PRT
<213> ORGANISM: Artificial
<220> FEATURE:
<223> OTHER INFORMATION: An artificially synthesized peptide

<400> SEQUENCE: 35

Lys Tyr Cys Pro Gly Gly Glu Leu Phe
1               5

<210> SEQ ID NO 36
<211> LENGTH: 9
<212> TYPE: PRT
<213> ORGANISM: Artificial
<220> FEATURE:
<223> OTHER INFORMATION: An artificially synthesized peptide

<400> SEQUENCE: 36

Arg Tyr Cys Pro Gly Gly Glu Leu Phe
1               5

<210> SEQ ID NO 37
<211> LENGTH: 9
<212> TYPE: PRT
<213> ORGANISM: Artificial
<220> FEATURE:
<223> OTHER INFORMATION: An artificially synthesized peptide

<400> SEQUENCE: 37

Glu Tyr Cys Pro Gly Gly Glu Leu Leu
1               5

<210> SEQ ID NO 38
<211> LENGTH: 9
<212> TYPE: PRT
<213> ORGANISM: Artificial
<220> FEATURE:
<223> OTHER INFORMATION: An artificially synthesized peptide

<400> SEQUENCE: 38

Glu Tyr Glu Pro Gly Gly Glu Leu Phe
1               5

<210> SEQ ID NO 39
<211> LENGTH: 9
<212> TYPE: PRT
<213> ORGANISM: Artificial
<220> FEATURE:
<223> OTHER INFORMATION: An artificially synthesized peptide

<400> SEQUENCE: 39

Glu Tyr Ile Pro Gly Gly Glu Leu Phe
1               5

<210> SEQ ID NO 40
<211> LENGTH: 9
<212> TYPE: PRT
<213> ORGANISM: Artificial
<220> FEATURE:
<223> OTHER INFORMATION: An artificially synthesized peptide

<400> SEQUENCE: 40

Glu Tyr Leu Pro Gly Gly Glu Leu Phe
1               5

<210> SEQ ID NO 41
<211> LENGTH: 9
<212> TYPE: PRT
<213> ORGANISM: Artificial
<220> FEATURE:
<223> OTHER INFORMATION: An artificially synthesized peptide

<400> SEQUENCE: 41

Glu Tyr Met Pro Gly Gly Glu Leu Phe
1               5

<210> SEQ ID NO 42
<211> LENGTH: 9
<212> TYPE: PRT
<213> ORGANISM: Artificial
<220> FEATURE:
<223> OTHER INFORMATION: An artificially synthesized peptide

<400> SEQUENCE: 42

Glu Tyr Asn Pro Gly Gly Glu Leu Phe
1               5

<210> SEQ ID NO 43
<211> LENGTH: 9
<212> TYPE: PRT
<213> ORGANISM: Artificial
<220> FEATURE:
<223> OTHER INFORMATION: An artificially synthesized peptide

<400> SEQUENCE: 43

Glu Tyr Pro Pro Gly Gly Glu Leu Phe
1               5

<210> SEQ ID NO 44
<211> LENGTH: 9
<212> TYPE: PRT
<213> ORGANISM: Artificial
<220> FEATURE:
<223> OTHER INFORMATION: An artificially synthesized peptide

<400> SEQUENCE: 44

Glu Tyr Cys Pro Gly Gly Asn Leu Phe
1               5

<210> SEQ ID NO 45
<211> LENGTH: 9
<212> TYPE: PRT
<213> ORGANISM: Artificial
<220> FEATURE:
<223> OTHER INFORMATION: An artificially synthesized peptide

```
<400> SEQUENCE: 45

Glu Tyr Cys Pro Gly Gly Gln Leu Phe
1               5

<210> SEQ ID NO 46
<211> LENGTH: 2501
<212> TYPE: DNA
<213> ORGANISM: Homo sapiens
<220> FEATURE:
<221> NAME/KEY: CDS
<222> LOCATION: (139)..(2094)

<400> SEQUENCE: 46
cgaaaagatt cttaggaacg ccgtaccagc cgcgtctctc aggacagcag gccctgtcc      60 ttctgtcggg cgccgctcag ccgtgccctc cgccctcag gttctttttc taattccaaa    120
taaacttgca agaggact atg aaa gat tat gat gaa ctt ctc aaa tat tat    171
                    Met Lys Asp Tyr Asp Glu Leu Leu Lys Tyr Tyr
                     1               5                  10 gaa tta cat gaa act att ggg aca ggt ggc ttt gca aag gtc aaa ctt    219
Glu Leu His Glu Thr Ile Gly Thr Gly Gly Phe Ala Lys Val Lys Leu
            15                  20                  25 gcc tgc cat atc ctt act gga gag atg gta gct ata aaa atc atg gat    267
Ala Cys His Ile Leu Thr Gly Glu Met Val Ala Ile Lys Ile Met Asp
        30                  35                  40 aaa aac aca cta ggg agt gat ttg ccc cgg atc aaa acg gag att gag    315
Lys Asn Thr Leu Gly Ser Asp Leu Pro Arg Ile Lys Thr Glu Ile Glu
    45                  50                  55 gcc ttg aag aac ctg aga cat cag cat ata tgt caa ctc tac cat gtg    363
Ala Leu Lys Asn Leu Arg His Gln His Ile Cys Gln Leu Tyr His Val
60                  65                  70                  75 cta gag aca gcc aac aaa ata ttc atg gtt ctt gag tac tgc cct gga    411
Leu Glu Thr Ala Asn Lys Ile Phe Met Val Leu Glu Tyr Cys Pro Gly
                80                  85                  90 gga gag ctg ttt gac tat ata att tcc cag gat cgc ctg tca gaa gag    459
Gly Glu Leu Phe Asp Tyr Ile Ile Ser Gln Asp Arg Leu Ser Glu Glu
            95                 100                 105 gag acc cgg gtt gtc ttc cgt cag ata gta tct gct gtt gct tat gtg    507
Glu Thr Arg Val Val Phe Arg Gln Ile Val Ser Ala Val Ala Tyr Val
        110                 115                 120 cac agc cag ggc tat gct cac agg gac ctc aag cca gaa aat ttg ctg    555
His Ser Gln Gly Tyr Ala His Arg Asp Leu Lys Pro Glu Asn Leu Leu
    125                 130                 135 ttt gat gaa tat cat aaa tta aag ctg att gac ttt ggt ctc tgt gca    603
Phe Asp Glu Tyr His Lys Leu Lys Leu Ile Asp Phe Gly Leu Cys Ala
140                 145                 150                 155 aaa ccc aag ggt aac aag gat tac cat cta cag aca tgc tgt ggg agt    651
Lys Pro Lys Gly Asn Lys Asp Tyr His Leu Gln Thr Cys Cys Gly Ser
                160                 165                 170 ctg gct tat gca gca cct gag tta ata caa ggc aaa tca tat ctt gga    699
Leu Ala Tyr Ala Ala Pro Glu Leu Ile Gln Gly Lys Ser Tyr Leu Gly
            175                 180                 185 tca gag gca gat gtt tgg agc atg ggc ata ctg tta tat gtt ctt atg    747
Ser Glu Ala Asp Val Trp Ser Met Gly Ile Leu Leu Tyr Val Leu Met
        190                 195                 200 tgt gga ttt cta cca ttt gat gat gat aat gta atg gct tta tac aag    795
Cys Gly Phe Leu Pro Phe Asp Asp Asp Asn Val Met Ala Leu Tyr Lys
    205                 210                 215 aag att atg aga gga aaa tat gat gtt ccc aag tgg ctc tct ccc agt    843
Lys Ile Met Arg Gly Lys Tyr Asp Val Pro Lys Trp Leu Ser Pro Ser
220                 225                 230                 235
```

```
agc att ctg ctt ctt caa caa atg ctg cag gtg gac cca aag aaa cgg      891
Ser Ile Leu Leu Leu Gln Gln Met Leu Gln Val Asp Pro Lys Lys Arg
        240                 245                 250 att tct atg aaa aat cta ttg aac cat ccc tgg atc atg caa gat tac      939
Ile Ser Met Lys Asn Leu Leu Asn His Pro Trp Ile Met Gln Asp Tyr
    255                 260                 265 aac tat cct gtt gag tgg caa agc aag aat cct ttt att cac ctc gat      987
Asn Tyr Pro Val Glu Trp Gln Ser Lys Asn Pro Phe Ile His Leu Asp
270                 275                 280 gat gat tgc gta aca gaa ctt tct gta cat cac aga aac aac agg caa     1035
Asp Asp Cys Val Thr Glu Leu Ser Val His His Arg Asn Asn Arg Gln
        285                 290                 295 aca atg gag gat tta att tca ctg tgg cag tat gat cac ctc acg gct     1083
Thr Met Glu Asp Leu Ile Ser Leu Trp Gln Tyr Asp His Leu Thr Ala
300                 305                 310                 315 acc tat ctt ctg ctt cta gcc aag aag gct cgg gga aaa cca gtt cgt     1131
Thr Tyr Leu Leu Leu Leu Ala Lys Lys Ala Arg Gly Lys Pro Val Arg
            320                 325                 330 tta agg ctt tct tct ttc tcc tgt gga caa gcc agt gct acc cca ttc     1179
Leu Arg Leu Ser Ser Phe Ser Cys Gly Gln Ala Ser Ala Thr Pro Phe
                335                 340                 345 aca gac atc aag tca aat aat tgg agt ctg gaa gat gtg acc gca agt     1227
Thr Asp Ile Lys Ser Asn Asn Trp Ser Leu Glu Asp Val Thr Ala Ser
            350                 355                 360 gat aaa aat tat gtg gcg gga tta ata gac tat gat tgg tgt gaa gat     1275
Asp Lys Asn Tyr Val Ala Gly Leu Ile Asp Tyr Asp Trp Cys Glu Asp
    365                 370                 375 gat tta tca aca ggt gct gct act ccc cga aca tca cag ttt acc aag     1323
Asp Leu Ser Thr Gly Ala Ala Thr Pro Arg Thr Ser Gln Phe Thr Lys
380                 385                 390                 395 tac tgg aca gaa tca aat ggg gtg gaa tct aaa tca tta act cca gcc     1371
Tyr Trp Thr Glu Ser Asn Gly Val Glu Ser Lys Ser Leu Thr Pro Ala
            400                 405                 410 tta tgc aga aca cct gca aat aaa tta aag aac aaa gaa aat gta tat     1419
Leu Cys Arg Thr Pro Ala Asn Lys Leu Lys Asn Lys Glu Asn Val Tyr
                415                 420                 425 act cct aag tct gct gta aag aat gaa gag tac ttt atg ttt cct gag     1467
Thr Pro Lys Ser Ala Val Lys Asn Glu Glu Tyr Phe Met Phe Pro Glu
            430                 435                 440 cca aag act cca gtt aat aag aac cag cat aag aga gaa ata ctc act     1515
Pro Lys Thr Pro Val Asn Lys Asn Gln His Lys Arg Glu Ile Leu Thr
    445                 450                 455 acg cca aat cgt tac act aca ccc tca aaa gct aga aac cag tgc ctg     1563
Thr Pro Asn Arg Tyr Thr Thr Pro Ser Lys Ala Arg Asn Gln Cys Leu
460                 465                 470                 475 aaa gaa act cca att aaa ata cca gta aat tca aca gga aca gac aag     1611
Lys Glu Thr Pro Ile Lys Ile Pro Val Asn Ser Thr Gly Thr Asp Lys
            480                 485                 490 tta atg aca ggt gtc att agc cct gag agg cgg tgc cgc tca gtg gaa     1659
Leu Met Thr Gly Val Ile Ser Pro Glu Arg Arg Cys Arg Ser Val Glu
                495                 500                 505 ttg gat ctc aac caa gca cat atg gag gag act cca aaa aga aag gga     1707
Leu Asp Leu Asn Gln Ala His Met Glu Glu Thr Pro Lys Arg Lys Gly
            510                 515                 520 gcc aaa gtg ttt ggg agc ctt gaa agg ggg ttg gat aag gtt atc act     1755
Ala Lys Val Phe Gly Ser Leu Glu Arg Gly Leu Asp Lys Val Ile Thr
    525                 530                 535 gtg ctc acc agg agc aaa agg aag ggt tct gcc aga gac ggg ccc aga     1803
Val Leu Thr Arg Ser Lys Arg Lys Gly Ser Ala Arg Asp Gly Pro Arg
```

```
                540           545          550         555
     aga cta aag ctt cac tat aat gtg act aca act aga tta gtg aat cca       1851
     Arg Leu Lys Leu His Tyr Asn Val Thr Thr Thr Arg Leu Val Asn Pro
                     560              565             570 gat caa ctg ttg aat gaa ata atg tct att ctt cca aag aag cat gtt       1899
     Asp Gln Leu Leu Asn Glu Ile Met Ser Ile Leu Pro Lys Lys His Val
                 575              580             585 gac ttt gta caa aag ggt tat aca ctg aag tgt caa aca cag tca gat       1947
     Asp Phe Val Gln Lys Gly Tyr Thr Leu Lys Cys Gln Thr Gln Ser Asp
                 590             595             600 ttt ggg aaa gtg aca atg caa ttt gaa tta gaa gtg tgc cag ctt caa       1995
     Phe Gly Lys Val Thr Met Gln Phe Glu Leu Glu Val Cys Gln Leu Gln
             605             610             615 aaa ccc gat gtg gtg ggt atc agg agg cag cgg ctt aag ggc gat gcc       2043
     Lys Pro Asp Val Val Gly Ile Arg Arg Gln Arg Leu Lys Gly Asp Ala
     620             625             630             635 tgg gtt tac aaa aga tta gtg gaa gac atc cta tct agc tgc aag gta       2091
     Trp Val Tyr Lys Arg Leu Val Glu Asp Ile Leu Ser Ser Cys Lys Val
                     640             645             650 taa ttgatggatt cttccatcct gccggatgag tgtgggtgtg atacagccta            2144
cataaagact gttatgatcg ctttgatttt aaagttcatt ggaactacca acttgtttct    2204
aaagagctat cttaagacca atatctcttt gttttaaac aaaagatatt attttgtgta     2264
tgaatctaaa tcaagcccat ctgtcattat gttactgtct tttttaatca tgtggttttg    2324
tatattaata attgttgact ttcttagatt cacttccata tgtgaatgta agctcttaac    2384
tatgtctctt tgtaatgtgt aatttctttc tgaaataaaa ccatttgtga atataaaaaa    2444
aaaaaaaaaa aaaaaaaaaa aaaaaaaaaa aaaaaaaaaa aaaaaaaaaa aaaaaaa       2501

<210> SEQ ID NO 47
<211> LENGTH: 651
<212> TYPE: PRT
<213> ORGANISM: Homo sapiens

<400> SEQUENCE: 47

Met Lys Asp Tyr Asp Glu Leu Leu Lys Tyr Tyr Glu Leu His Glu Thr
1               5                   10                  15

Ile Gly Thr Gly Gly Phe Ala Lys Val Lys Leu Ala Cys His Ile Leu
            20                  25                  30

Thr Gly Glu Met Val Ala Ile Lys Ile Met Asp Lys Asn Thr Leu Gly
        35                  40                  45

Ser Asp Leu Pro Arg Ile Lys Thr Glu Ile Glu Ala Leu Lys Asn Leu
    50                  55                  60

Arg His Gln His Ile Cys Gln Leu Tyr His Val Leu Glu Thr Ala Asn
65                  70                  75                  80

Lys Ile Phe Met Val Leu Glu Tyr Cys Pro Gly Gly Glu Leu Phe Asp
                85                  90                  95

Tyr Ile Ile Ser Gln Asp Arg Leu Ser Glu Glu Thr Arg Val Val
            100                 105                 110

Phe Arg Gln Ile Val Ser Ala Val Ala Tyr Val His Ser Gln Gly Tyr
        115                 120                 125

Ala His Arg Asp Leu Lys Pro Glu Asn Leu Leu Phe Asp Glu Tyr His
    130                 135                 140

Lys Leu Lys Leu Ile Asp Phe Gly Leu Cys Ala Lys Pro Lys Gly Asn
145                 150                 155                 160

Lys Asp Tyr His Leu Gln Thr Cys Cys Gly Ser Leu Ala Tyr Ala Ala
```

```
                165                 170                 175
Pro Glu Leu Ile Gln Gly Lys Ser Tyr Leu Gly Ser Glu Ala Asp Val
            180                 185                 190

Trp Ser Met Gly Ile Leu Leu Tyr Val Leu Met Cys Gly Phe Leu Pro
        195                 200                 205

Phe Asp Asp Asn Val Met Ala Leu Tyr Lys Lys Ile Met Arg Gly
    210                 215                 220

Lys Tyr Asp Val Pro Lys Trp Leu Ser Pro Ser Ser Ile Leu Leu Leu
225                 230                 235                 240

Gln Gln Met Leu Gln Val Asp Pro Lys Lys Arg Ile Ser Met Lys Asn
                245                 250                 255

Leu Leu Asn His Pro Trp Ile Met Gln Asp Tyr Asn Tyr Pro Val Glu
            260                 265                 270

Trp Gln Ser Lys Asn Pro Phe Ile His Leu Asp Asp Asp Cys Val Thr
        275                 280                 285

Glu Leu Ser Val His His Arg Asn Asn Arg Gln Thr Met Glu Asp Leu
    290                 295                 300

Ile Ser Leu Trp Gln Tyr Asp His Leu Thr Ala Thr Tyr Leu Leu Leu
305                 310                 315                 320

Leu Ala Lys Lys Ala Arg Gly Lys Pro Val Arg Leu Arg Leu Ser Ser
                325                 330                 335

Phe Ser Cys Gly Gln Ala Ser Ala Thr Pro Phe Thr Asp Ile Lys Ser
            340                 345                 350

Asn Asn Trp Ser Leu Glu Asp Val Thr Ala Ser Asp Lys Asn Tyr Val
        355                 360                 365

Ala Gly Leu Ile Asp Tyr Asp Trp Cys Glu Asp Leu Ser Thr Gly
    370                 375                 380

Ala Ala Thr Pro Arg Thr Ser Gln Phe Thr Lys Tyr Trp Thr Glu Ser
385                 390                 395                 400

Asn Gly Val Glu Ser Lys Ser Leu Thr Pro Ala Leu Cys Arg Thr Pro
                405                 410                 415

Ala Asn Lys Leu Lys Asn Lys Glu Asn Val Tyr Thr Pro Lys Ser Ala
            420                 425                 430

Val Lys Asn Glu Glu Tyr Phe Met Phe Pro Glu Pro Lys Thr Pro Val
        435                 440                 445

Asn Lys Asn Gln His Lys Arg Glu Ile Leu Thr Thr Pro Asn Arg Tyr
    450                 455                 460

Thr Thr Pro Ser Lys Ala Arg Asn Gln Cys Leu Lys Glu Thr Pro Ile
465                 470                 475                 480

Lys Ile Pro Val Asn Ser Thr Gly Thr Asp Lys Leu Met Thr Gly Val
                485                 490                 495

Ile Ser Pro Glu Arg Arg Cys Arg Ser Val Glu Leu Asp Leu Asn Gln
            500                 505                 510

Ala His Met Glu Glu Thr Pro Lys Arg Lys Gly Ala Lys Val Phe Gly
        515                 520                 525

Ser Leu Glu Arg Gly Leu Asp Lys Val Ile Thr Val Leu Thr Arg Ser
    530                 535                 540

Lys Arg Lys Gly Ser Ala Arg Asp Gly Pro Arg Arg Leu Lys Leu His
545                 550                 555                 560

Tyr Asn Val Thr Thr Thr Arg Leu Val Asn Pro Asp Gln Leu Leu Asn
                565                 570                 575

Glu Ile Met Ser Ile Leu Pro Lys Lys His Val Asp Phe Val Gln Lys
            580                 585                 590
```

Gly Tyr Thr Leu Lys Cys Gln Thr Gln Ser Asp Phe Gly Lys Val Thr
            595                 600                 605

Met Gln Phe Glu Leu Glu Val Cys Gln Leu Gln Lys Pro Asp Val Val
        610                 615                 620

Gly Ile Arg Arg Gln Arg Leu Lys Gly Asp Ala Trp Val Tyr Lys Arg
625                 630                 635                 640

Leu Val Glu Asp Ile Leu Ser Ser Cys Lys Val
                645                 650

<210> SEQ ID NO 48
<211> LENGTH: 10
<212> TYPE: PRT
<213> ORGANISM: Artificial
<220> FEATURE:
<223> OTHER INFORMATION: An artificially synthesized peptide

<400> SEQUENCE: 48

Arg Tyr Leu Arg Gln Gln Leu Leu Gly Ile
1               5                   10

<210> SEQ ID NO 49
<211> LENGTH: 22
<212> TYPE: DNA
<213> ORGANISM: Artificial
<220> FEATURE:
<223> OTHER INFORMATION: Artificial sequence

<400> SEQUENCE: 49
gtctaccagg cattcgcttc at                                      22

<210> SEQ ID NO 50
<211> LENGTH: 24
<212> TYPE: DNA
<213> ORGANISM: Artificial
<220> FEATURE:
<223> OTHER INFORMATION: Artificial sequence

<400> SEQUENCE: 50
tcagctggac cacagccgca gcgt                                    24

<210> SEQ ID NO 51
<211> LENGTH: 21
<212> TYPE: DNA
<213> ORGANISM: Artificial
<220> FEATURE:
<223> OTHER INFORMATION: Artificial sequence

<400> SEQUENCE: 51
tcagaaatcc tttctcttga c                                       21

<210> SEQ ID NO 52
<211> LENGTH: 24
<212> TYPE: DNA
<213> ORGANISM: Artificial
<220> FEATURE:
<223> OTHER INFORMATION: Artificial sequence

<400> SEQUENCE: 52
ctagcctctg gaatcctttc tctt                                    24

MODIFIED MELK PEPTIDES AND VACCINES CONTAINING THE SAME

PRIORITY

The present application is a U.S. National Phase of PCT/JP2011/000352, filed Jan. 24, 2011, which claims the benefit of U.S. Provisional Application No. 61/297,996, filed on Jan. 25, 2010, the contents of which are hereby incorporated herein by reference in their entirety for all purposes.

The present invention relates to the field of biological science, more specifically to the field of cancer therapy. In particular, the present invention relates to novel peptides that are extremely effective as cancer vaccines, as well as drugs for treating and preventing tumors (or diseases relating to MELK overexpression).

REFERENCE TO SEQUENCE LISTING

This application includes a Sequence Listing as a text file named "87331-021910US-845272_SEQLIST.txt" created Jul. 23, 2012, and containing 26,299 bytes. The material contained in this text file is incorporated by reference in its entirety for all purposes.

BACKGROUND ART

It has been demonstrated that CD8 positive cytotoxic T lymphocytes (CTLs) recognize epitope peptides derived from the tumor-associated antigens (TAAs) found on the major histocompatibility complex (MHC) class I molecule, and then kill the tumor cells. Since the discovery of the melanoma antigen (MAGE) family as the first example of TAAs, many other TAAs have been discovered primarily through immunological approaches (NPLs 1, 2). Some of these TAAs are currently undergoing clinical development as immunotherapeutic targets.

Favorable TAAs are indispensable for proliferation and survival of cancer cells. The use of such TAAs as targets for immunotherapy may minimize the well-described risk of immune escape of cancer cells attributable to deletion, mutation, or down-regulation of TAAs as a consequence of therapeutically driven immune selection. Accordingly, the identification of new TAAs capable of inducing potent and specific anti-tumor immune responses, warrants further development and clinical investigation of peptide vaccination strategies for various types of cancer (NPLs 3-10). To date, there have been several clinical reports of trials using these TAA derived peptides (NPLs 11-13). Although some success has been observed, there remains a need for new TAAs as immunotherapeutic targets.

MELK, maternal embryonic leucine zipper kinase, has been previously identified as a new member of the snf1/AMPK serine-threonine kinase family that is involved in mammalian embryonic development (NPL 14). This gene has been shown to play an important role in stem cell renewal (NPL 15), cell-cycle progression (NPL 16, 17) and pre-mRNA splicing (NPL 18). To that end, through gene expression profiling with a genome-wide cDNA microarray containing 23,040 genes, the present inventors have been identified MELK which is up-regulated in breast cancer (NPL 19).

MELK is up-regulated in several cancer cells, for example, lung, bladder, lymphoma and cervical cancer cells. Northern blot analysis on multiple human tissues and cancer cell lines demonstrated that MELK was overexpressed at a significantly high level in a great majority of breast cancers and cell lines, but was not expressed in normal vital organs such as heart, liver, lung and kidney. Furthermore, suppression of MELK expression by siRNA has significantly been shown to result in growth of human breast cancer cells.

Multiple investigations has been reported on modifying the amino acid residue of the peptides that are crucial for the interaction with the MHC or the T cell receptor to enhance the immunogenicity of the peptides (NPL 20, 21).

CITATION LIST

Patent Literature

[PTL 1] WO2005/073374

Non Patent Literature

[NPL 1] Boon T, Int J Cancer 1993 May 8, 54(2): 177-80
[NPL 2] Boon T & van der Bruggen P, J Exp Med 1996 Mar. 1, 183(3): 725-9
[NPL 3] Harris C C, J Natl Cancer Inst 1996 Oct. 16, 88(20): 1442-55
[NPL 4] Butterfield L H et al., Cancer Res 1999 Jul. 1, 59(13): 3134-42
[NPL 5] Vissers J L et al., Cancer Res 1999 Nov. 1, 59(21): 5554-9
[NPL 6] van der Burg S H et al., J Immunol 1996 May 1, 156(9): 3308-14
[NPL 7] Tanaka F et al., Cancer Res 1997 Oct. 15, 57(20): 4465-8
[NPL 8] Fujie T et al., Int J Cancer 1999 Jan. 18, 80(2): 169-72
[NPL 9] Kikuchi M et al., Int J Cancer 1999 May 5, 81(3): 459-66
[NPL 10] Oiso M et al., Int J Cancer 1999 May 5, 81(3): 387-94
[NPL 11] Belli F et al., J Clin Oncol 2002 Oct. 15, 20(20): 4169-80
[NPL 12] Coulie P G et al., Immunol Rev 2002 October, 188: 33-42
[NPL 13] Rosenberg S A et al., Nat Med 2004 September, 10(9): 909-15
[NPL 14] Heyer B S et al., Dev Dyn. 1999 August 215(4): 344-51
[NPL 15] Nakano I et al., J Cell Biol. 2005 Aug. 1, 170(3): 413-27)
[NPL 16] Blot J et al., Dev Biol. 2002 Jan. 15, 241(2):327-38
[NPL 17] Seong H A et al., Biochem J. 2002 Feb. 1, 361(Pt 3):597-604
[NPL 18] Vulsteke V et al., J Biol. Chem. 2004 Mar. 5, 279(10):8642-7. Epub 2003 Dec. 29
[NPL 19] Lin M L et al., Breast Cancer Res. 2007; 9 (1):R17
[NPL 20] Valmori D, et al., J Immunol. 1998 Feb. 15; 160(4): 1750-8
[NPL 21] Salazar E, et al., Int J Cancer. 2000 Mar. 15; 85(6): 829-38

SUMMARY OF INVENTION

The present invention is based, in part, on the discovery of novel peptides that may serve as suitable targets of immunotherapy. Because TAAs are generally perceived for the immune system as "self" and therefore often have no immunogenicity, the discovery of appropriate targets is of extreme importance. Recognizing that MELK (as described, for example, in SEQ ID NO: 47) (encoded by the gene of GenBank Accession No. NM_014791 (SEQ ID NO: 46)) has been identified as up-regulated in tissues of endometriosis and cancers including but not limited to breast cancer, bladder cancer, cervical cancer, cholangiocellular carcinoma, chronic myeloid leukemia (CML), colorectal cancer, esophagus cancer, gastric cancer, liver cancer, non-small cell lung cancer (NSCLC), lymphoma, osteosarcoma, ovarian cancer, pancreatic cancer, prostate cancer, renal carcinoma and small cell lung cancer (SCLC) (WO2010/013485), the present invention focuses on MELK as a target of cancer immunotherapy.

To that end, the present invention is directed at least in part, to the identification of specific modified epitope peptides of MELK that possess the ability to induce cytotoxic T lymphocytes (CTLs) specific to MELK. As discussed in detail below, peripheral blood mononuclear cells (PBMCs) obtained from healthy donors were stimulated using A*2402 binding candidate peptides derived from modified MELK epitope peptide, i.e., wild type MELK-A24-9-87_WT (SEQ ID NO: 6). CTL lines with specific cytotoxicity against HLA-A24 positive target cells pulsed with each of candidate peptides were then established. Taken together, these results demonstrate that these peptides are HLA-A24 restricted epitope peptides that can induce potent and specific immune responses against cells expressing MELK. The results further demonstrate that MELK is strongly immunogenic and that the epitopes thereof are effective targets for tumor immunotherapy.

Accordingly, it is an object of the present invention to provide isolated peptides of the modified epitope peptide derived from MELK (SEQ ID NO: 47), specifically the modified epitope peptide of wild type MELK-A24-9-87_WT (SEQ ID NO: 6), or immunologically active fragments thereof that bind to HLA antigens. The present peptides have CTL inducibility. Thus, they can be used to induce CTL ex vivo or can be administered to a subject for inducing immune responses against endometriosis and cancers, examples of which include, but are not limited to, breast cancer, bladder cancer, cervical cancer, cholangiocellular carcinoma, CML, colorectal cancer, cancer, gastric cancer, liver cancer, NSCLC, lymphoma, osteosarcoma, ovarian cancer, pancreatic cancer, prostate cancer, renal carcinoma and SCLC. Preferred peptides are nonapeptides, and typically, consist of the amino acid sequence selected from the group consisting of SEQ ID NOs: 35-45. Of these, the peptides having an amino sequence selected from among SEQ ID NOs: 35, 41 and 44 showed particularly strong CTL inducibility and thus are particularly useful in the present invention.

The present invention also contemplates modified peptides, having an amino acid sequence of SEQ ID NOs: 35-45, wherein one, two or more amino acid(s) is/are substituted, deleted or added, so long as the modified peptides retain the requisite original CTL inducibility of the original peptide.

Further, the present invention provides isolated polynucleotides encoding any of the peptides of the present invention. These polynucleotides can be used to induce antigen-expressing cells (APCs) with CTL inducibility, like the peptides of the present invention, or can be administered to a subject for inducing immune responses against cancers.

When administered to a subject, the present peptides are presented on the surface of APCs so as to induce CTLs targeting the respective peptides. Therefore, it is an object of the present invention to provide substances that induce CTLs, such substances including one or more peptides of the present invention or polynucleotides encoding such peptides. The present invention further contemplates pharmaceutical substances including one or more of the peptides of the present invention or polynucleotides encoding such peptides, such compositions can be used for treating and/or for the prophylaxis of endometriosis and cancers, such cancers including, but not limited, breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC, and/or for preventing postoperative recurrence thereof. Thus, it is yet another object of the present invention to provide pharmaceutical composition or substances formulated for the treatment and/or prevention of endometriosis or cancer, and/or prevention of postoperative recurrence thereof and including any of the peptides or polynucleotides of the present invention. Instead of or in addition to the present peptides or polynucleotides, the present substances or pharmaceutical of the present invention substances may optionally include, as the active ingredient, APCs or exosomes which present any of the peptides of the present invention.

The peptides and polynucleotides of the present invention may be used to induce APCs that present on the surface a complex of an HLA antigen and a present peptide, for example, by contacting APCs derived from a subject with the present peptide or introducing a polynucleotide encoding the present peptide into APCs. Such APCs have high CTL inducibility against the target peptides and thus are useful for cancer immunotherapy. Accordingly, it is another object of the present invention to provide methods for inducing APCs with CTL inducibility as well as APCs obtained by such methods.

It is a further object of the present invention to provide methods for inducing CTL, methods that includes the step of co-culturing CD8-positive cells with APCs or exosomes presenting a peptide of the present invention on its surface or the step of introducing a gene that includes a polynucleotide encoding a T cell receptor (TCR) subunit binding to the present peptide. CTLs obtainable by the present methods also find utility in the treatment and/or preventing diseases in which MELK is overexpressed, such as endometriosis, breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC, but are not limited to. Therefore, it is another object of the present invention to provide CTLs obtained by the present methods.

Moreover, a further object of the present invention is to provide methods for inducing an immune response against cancer in a subject in need thereof, such methods including the step of administering to the subject a substance or a composition containing modified MELK or immunologically active fragments thereof, polynucleotides encoding modified MELK or the fragments thereof, and exosomes or APCs presenting modified MELK or the fragments thereof.

The applicability of the present invention extends to any of a number of diseases relating to or arising from MELK overexpression including endometriosis and cancer, examples of which include, but are not limited to, breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC.

More specifically, the present invention provides followings:

[1] An isolated peptide binding to HLA antigen and having cytotoxic T lymphocyte (CTL) inducibility, wherein the peptide consists of the amino acid sequence of SEQ ID NO: 6 or consists of an amino acid sequence comprising one or more amino acid substitutions in the amino acid sequence of SEQ ID NO: 6,

[2] The isolated peptide of [1], wherein the HLA antigen is HLA-A24,
[3] The isolated peptide of [1], wherein the polypeptide comprises one or more amino acid substitutions at the positions selected from the group consisting of (a)-(d) in the amino acid sequence of SEQ ID NO: 6:
(a) N-terminal amino acid,
(b) third amino acid from the N-terminus,
(c) third amino acid from the C-terminus and
(d) C-terminal amino acid,
[4] The isolated peptide of [3], wherein the polypeptide comprises one or more amino acid substitutions selected from the group consisting of (i) to (iv):
(i) amino acid substitution from E to K or R at the N-terminal amino acid in the amino acid sequence of SEQ ID NO: 6,
(ii) amino acid substitution from C to E, I, L, M, N or P at the third amino acid from the N-terminus in the amino acid sequence of SEQ ID NO: 6,
(iii) amino acid substitution from E to N or Q at the third amino acid from the C-terminus in the amino acid sequence of SEQ ID NO: 6 and
(iv) amino acid substitution from F to L at the C-terminal amino acid in the amino acid sequence of SEQ ID NO: 6,
[5] The isolated peptide of [4], wherein the peptide comprises a single amino acid substitution,
[6] The isolated peptide of [4], wherein the peptide comprises two amino acid substitutions,
[7] The isolated peptide of [4], wherein the peptide comprises three amino acid substitutions,
[8] The isolated peptide of [4], wherein the peptide comprises four amino acid substitutions,
[9] The isolated peptide of [4]-[5], which comprises an amino acid sequence selected from the group consisting of SEQ ID NOs: 35-45,
[10] An isolated peptide binding to HLA antigen and having cytotoxic T lymphocyte (CTL) inducibility, wherein the said peptide consists of an amino acid sequence selected from the group consisting of SEQ ID NOs: 35-45, wherein 1, 2, or several amino acid(s) are inserted, substituted, deleted or added,
[11] The peptide of [10] having one or both of the following characteristics:
(a) the second amino acid from the N-terminus is selected from the group of phenylalanine, tyrosine, methionine and tryptophan; and
(b) the C-terminal amino acid is selected from the group of phenylalanine, leucine, isoleucine, tryptophan and methionine,
[12] An isolated polynucleotide encoding a peptide of any one of [1] to [11],
[13] A substance for inducing CTL, wherein the substance comprises one or more peptide(s) of any one of [1] to [11], or one or more polynucleotide(s) of [12],
[14] A pharmaceutical composition for the treatment and/or prophylaxis of cancers or endometriosis, and/or the prevention of postoperative recurrence thereof, wherein the composition comprises one or more peptide(s) of any one of [1] to [11], or one or more polynucleotide(s) of [12],
[15] The pharmaceutical composition of [14], wherein said composition is formulated for the administration to a subject whose HLA antigen is HLA-A24,
[16] The pharmaceutical composition of [14] or [15], wherein said composition is formulated for treating cancer or endometriosis,
[17] A method for inducing an antigen-presenting cell (APC) with CTL inducibility, wherein the method comprises one of the following steps:
(a) contacting an APC with a peptide of any one of [1] to [11] in vitro, ex vivo or in vivo; and
(b) introducing a polynucleotide encoding a peptide of any one of [1] to [9] into an APC,
[18] A method for inducing CTL by any of the methods comprising at least one of the following steps:
(a) co-culturing CD8-positive T cells with APCs, which presents on its surface a complex of an HLA antigen and a peptide of any one of [1] to [11];
(b) co-culturing CD8-positive T cells with exosomes, which presents on its surface a complex of an HLA antigen and a peptide of any one of [1] to [11]; and
(c) introducing a gene that comprises a polynucleotide encoding a T cell receptor (TCR) subunit polypeptide binding to a peptide of any one of [1] to [9] into a T cell,
[19] An isolated APC that presents on its surface a complex of an HLA antigen and a peptide of any one of [1] to [11],
[20] The APC of [19], wherein said APC is induced by the method of [17],
[21] An isolated CTL that targets a peptide of any one of [1] to [11],
[22] The CTL of [21], which is induced by the method of [18], and
[23] A method of inducing immune response against cancer or endometriosis in a subject comprising administering to the subject a composition comprising a peptide of any one of [1] to [11], an immunologically active fragment thereof, or a polynucleotide encoding the peptide or the fragment.

It is to be understood that both the foregoing summary of the invention and the following detailed description are of exemplified embodiments, and not restrictive of the invention or other alternate embodiments of the invention.

In addition to the above, other objects and features of the invention will become more fully apparent when the following detailed description is read in conjunction with the accompanying figures and examples. However, it is to be understood that both the foregoing summary of the invention and the following detailed description are of exemplified embodiments, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures, and the detailed description of the present invention and its preferred embodiments which follows.

FIG. 5B depicts the photographs showing the result of IFN-gamma ELISPOT assays on CTLs of donor C induced with modified peptides from MELK-A24-9-87_WT (SEQ ID NO: 6). The CTLs stimulated with MELK-A24-9-87_7N (SEQ ID NO: 44) (a) showed potential IFN-gamma productive ability. On the other hand, the peptide specific IFN-gamma production was not detected from the CTLs stimulated with MELK-A24-9-87_WT (SEQ ID NO: 6) (b). In the figures, "+" indicates the IFN-gamma production against the target cells pulsed with cognate peptides, and "−" indicates the IFN-gamma production against target cells not pulsed with any peptides. The cells in the well number #14 stimulated with MELK-A24-9-87_7N (SEQ ID NO: 44) were expanded to establish CTL lines. The cells in the well number #4 stimulated with MELK-A24-9-87_WT (SEQ ID NO: 6) that showed minor IFN-gamma production were also expanded.

In FIG. 9 (a), "black lozenge" indicates the IFN-gamma production against target cells pulsed with MELK-A24-9-199 (SEQ ID NO: 1) and "white square" indicates the IFN-gamma production against target cells not pulsed with any peptides. In FIG. 9 (b), the IFN-gamma production against the tumor cell lines that expressed both MELK and HLA-A*2402 (black lozenge; KLM-1) and that expressed MELK but not expressed HLA-A*2402 (white square; KP-1N).

DESCRIPTION OF EMBODIMENTS

Figure 1:
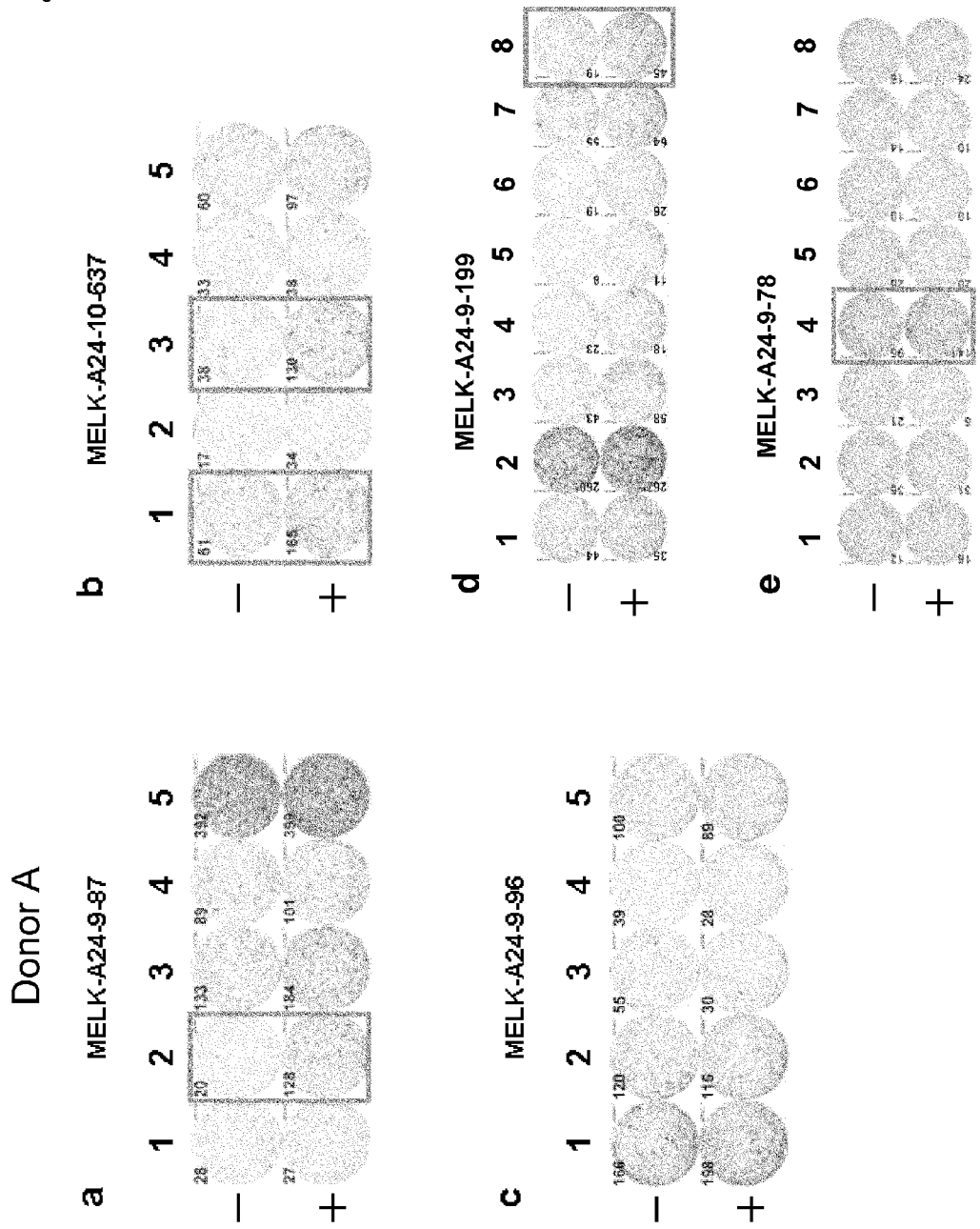
FIG. 1 depicts the photographs showing the result of IFN-gamma ELISPOT assays on CTLs of donor A induced with peptides derived from MELK. The CTLs stimulated with MELK-A24-9-87 (SEQ ID NO: 6) (a) MELK-A24-10-637 (SEQ ID NO: 23) (b) MELK-A24-9-199 (SEQ ID NO: 1) (d) and MELK-A24-9-78 (SEQ ID NO: 21) (e) showed potential IFN-gamma productive ability. In contrast, as typical case of negative data, specific IFN-gamma production was not shown from the CTLs stimulated with MELK-A24-9-96 (SEQ ID NO: 2) (c). In the figures, "+" indicates the IFN-gamma production against the target cells pulsed with cognate peptides, and "−" indicates the IFN-gamma production against target cells not pulsed with any peptides.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue or prior invention.

Unless otherwise defined, all technical and scientific terms used herein have the same meaning as commonly understood by one of ordinary skill in the art to which the present invention belongs. In case of conflict, the present specification, including definitions, will control. In addition, the materials, methods, and examples are illustrative only and not intended to be limiting.

I. DEFINITIONS

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "oligopeptide" sometimes used in the present specification is used to refer to peptides of the present invention which are 20 residues or fewer, typically 15 residues or fewer in length and is typically composed of between about 8 and about 11 residues, often 9 or 10 residues.

The term "amino acid" as used herein refers to naturally occurring and synthetic amino acids, as well as amino acid analogs and amino acid mimetics that similarly function to the naturally occurring amino acids. Amino acids can be either L-amino acids or D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotide", "nucleotide" and "nucleic acid" are used interchangeably herein and, unless otherwise specifically indicated are similarly to the amino acids referred to by their commonly accepted single-letter codes.

The term "composition", "substance" or "agent" are used as interchangeably herein to refer to a product that includes the specified ingredients in the specified amounts, as well as any product which results, directly or indirectly, from combination of the specified ingredients in the specified amounts. Such term in relation to "pharmaceutical composition", is intended to encompass a product including the active ingredient(s), and any inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, in the context of the present invention, the term "pharmaceutical composition" refers to any composition made by admixing a compound of the present invention and a pharmaceutically or physiologically acceptable carrier. The phrase "pharmaceutically acceptable carrier" or "physiologically acceptable carrier", as used herein, means a pharmaceutically or physiologically acceptable material, composition, substance or vehicle, including but not limited to, a liquid or solid filler, diluent, excipient, solvent or encapsulating material, involved in carrying or transporting the subject scaffolded polypharmacophores from one organ, or portion of the body, to another organ, or portion of the body.

The term "active ingredient" herein refers to a substance in an agent or composition that is biologically or physiologically active. Particularly, in a pharmaceutical agent or composition, "active ingredient" refers to a substance that shows an objective pharmacological effect. For example, in case of pharmaceutical agents or compositions for use in the treatment or prevention of cancer, active ingredients in the agents or compositions may lead to at least one biological or physiologically action on cancer cells and/or tissues directly or indirectly. Preferably, such action may include reducing or inhibiting cancer cell growth, damaging or killing cancer cells and/or tissues, and so on. Typically, indirect effect of active ingredients is inductions of CTLs recognizing or killing cancer cells. Before formulated, "active ingredient" is also referred to as "bulk", "drug substance" or "technical product".

The pharmaceutical agents or compositions of the present invention find particular use as vaccines. In the context of the present invention, the phrase "vaccine" (also referred to as an "immunogenic composition") refers to a substance that has the function to induce anti-tumor immunity upon inoculation into animals.

Unless otherwise defined, the term "cancer" refers to the cancers over expressing MELK gene, examples of which include, but are not limited to, breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC.

Unless otherwise defined, the term "endometriosis" refers to the endometriosis over expressing MELK gene, examples of which include, but are not limited to, stage I (Minimal), II (Mild), III (Moderate), or IV (Severe) of the endometriosis classified by the revised American Fertility Society classification. Alternatively, examples of the endometriosis include, but are not limited to, stage I, II, III, or IV of the endometriosis classified by the Beecham classification.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor cells, virus-infected cells) and inducing the death of such cells.

Unless otherwise defined, the term "HLA-A24" refers to the HLA-A24 type containing the subtypes such as HLA-A*2402.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

As used herein, in the context of a subject or patient, the phrase "HLA-A24 positive" refers to that the subject or patient homozygously or heterozygously possess HLA-A24 antigen gene, and HLA-A24 antigen is expressed in cells of the subject or patient as an HLA antigen.

To the extent that the methods and compositions of the present invention find utility in the context of the "treatment" of cancer or endometriosis, a treatment is deemed "efficacious" if it leads to clinical benefit such as, reduction in expression of a MELK gene, or a decrease in size, prevalence, or metastatic potential of the cancer or endometriosis in the subject. When the treatment is applied prophylactically, "efficacious" means that it retards or prevents cancers or endometriosis from forming or prevents or alleviates a clinical symptom of cancer or other disease. Efficaciousness is determined in association with any known method for diagnosing or treating a disease or the particular tumor type.

To the extent that the methods and compositions of the present invention find utility in the context of the "prevention" and "prophylaxis" of diseases such as cancer or endometriosis, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

In the context of the present invention, the treatment and/or prophylaxis of cancer or endometriosis and/or the prevention of postoperative recurrence thereof may include one or more of the following steps, the surgical removal of cancer cells, the inhibition of the growth of cancerous cells, the involution or regression of a tumor, the induction of remission and suppression of occurrence of cancer, the tumor regression, and the reduction or inhibition of metastasis. Effective treatment and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g., bispecific antibodies) formed from at least two intact antibodies, and antibody fragments so long as they exhibit the desired biological activity. An "antibody" indicates all classes (e.g., IgA, IgD, IgE, IgG and IgM).

II. PEPTIDES

To demonstrate that modified peptides derived from MELK function as an antigen recognized by CTLs, modified peptides derived from MELK-A24-9-87_WT (SEQ ID NO: 6) were analyzed to determine whether they were antigen epitopes restricted by HLA-A24 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994).

Candidates of HLA-A24 binding modified peptides derived from MELK, that have the potential ability to induce specific CTLs more efficiently than wild type MELK-A24-9-87 (MELK-A24-9-87_WT) (SEQ ID NO: 6), were identified based on their binding affinities to HLA-A24. That is, according to the present invention, modified peptides contain the amino acid sequence having one or more amino acid substitution in the amino acid sequence of SEQ ID NO: 6 are provided.

In the present invention, the number of amino acid substitution in the modified peptides of the MELK-A24-9-87_WT (SEQ ID NO: 6) is at least one. In some embodiments, the number of the substitutions is one, two, three, or four substitutions at the following positions (a)-(d) in the amino acid sequence of SEQ ID NO: 6.
(a) N-terminal amino acid,
(b) third amino acid from the N-terminus
(c) third amino acid from the C-terminus and
(d) C-terminal amino acid.

The positions of the conserved residues in the sequences of peptides displayed by binding to HLA antigens are already known (J Immunol 1994, 152: 3913; Immuno-genetics 1995, 41: 178; J Immunol 1994, 155: 4307). In accordance with the conserved residues, substitutions at the second amino acid from the N-terminus and C-terminus amino acid may be introduced to maintain or increase the HLA-A24 binding with the peptides. However, the positions shown as (a)-(d) are different from the positions of the conserved residues. In other words, the present invention provides modified peptides having the improved CTL inducibility with substitutions different from the previously-known conserved residues.

In an embodiment of the present invention, substitutions at these positions may be selected from the group consisting of (i) to (iv):

(i) amino acid substitution from E to K or R at the N-terminal amino acid in the amino acid sequence of SEQ ID NO: 6,
(ii) amino acid substitution from C to E, I, L, M, N or P at the third amino acid from the N-terminus in the amino acid sequence of SEQ ID NO: 6,
(iii) amino acid substitution from E to N or Q at the third amino acid from the C-terminus in the amino acid sequence of SEQ ID NO: 6 and
(iv) amino acid substitution from F to L at the C-terminal amino acid in the amino acid sequence of SEQ ID NO: 6.

The modification of one, two or more amino acids in a peptide will not influence the function of the peptide as described in detail below. The following peptides were identified as the candidate peptides having higher binding ability compared to MELK-A24-9-87_WT (SEQ ID NO: 6):

MELK-A24-9-87_1K (SEQ ID NO: 35),
MELK-A24-9-87_1R (SEQ ID NO: 36),
MELK-A24-9-87_9L (SEQ ID NO: 37),
MELK-A24-9-87_3E (SEQ ID NO: 38),
MELK-A24-9-87_3I (SEQ ID NO: 39),
MELK-A24-9-87_3L (SEQ ID NO: 40),
MELK-A24-9-87_3M (SEQ ID NO: 41),
MELK-A24-9-87_3N (SEQ ID NO: 42),
MELK-A24-9-87_3P (SEQ ID NO: 43),
MELK-A24-9-87_7N (SEQ ID NO: 44), and
MELK-A24-9-87_7Q (SEQ ID NO: 45).

After in vitro stimulation of T-cells by dendritic cells (DCs) loaded with these peptides, CTLs were successfully established using the following peptides:

MELK-A24-9-87_1K (SEQ ID NO: 35),
MELK-A24-9-87_3M (SEQ ID NO: 41), and
MELK-A24-9-87_7N (SEQ ID NO: 44).

These established CTLs show potent specific CTL activity against target cells pulsed with respective peptides. The results herein demonstrate that the peptides are modified epitope peptides of MELK restricted by HLA-A24.

Since the MELK gene is over expressed in endometriosis and cancer cells and tissues, including, but not limited to, those of breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC but is not expressed in most normal organs, it is a good target for immunotherapy. Thus, the present invention provides nonapeptides (peptides composed of nine amino acid residues) corresponding to CTL-recognized modified epitopes of MELK. Preferred examples of nonapeptides of the present invention include those peptides having an the amino acid sequence selected from among SEQ ID NOs: 35-45.

Generally, software programs presently available on the Internet, such as those described in Parker K C et al., J Immunol 1994 Jan. 1, 152(1): 163-75, can be used to calculate the binding affinities between various peptides and HLA antigens in silico. Binding affinity with HLA antigens can be measured as described, for example, in the references to Parker K C et al., J Immunol 1994 Jan. 1, 152(1): 163-75; and Kuzushima K et al., Blood 2001, 98(6): 1872-81, Larsen M V et al. BMC Bioinformatics. 2007 Oct. 31; 8: 424, Buus S et al. Tissue Antigens., 62:378-84, 2003, Nielsen M et al., Protein Sci 2003; 12: 1007-17, and Nielsen M et al. PLoS ONE 2007; 2: e796, which are summarized in, e.g., Lafuente E M et al., Current Pharmaceutical Design, 2009, 15, 3209-3220. Methods for determining binding affinity are described, for example, in the Journal of Immunological Methods, 1995, 185: 181-190 and Protein Science, 2000, 9: 1838-1846.

Therefore, one can use such software programs to select immunologically active fragments derived from MELK that have high binding affinity with HLA antigens. Accordingly, the present invention encompasses peptides composed of any immunologically active fragments derived from modified MELK that bind with HLA antigens identified using such known programs.

The peptides of the present invention can be flanked with additional amino acid residues so long as the resulting peptide retains its CTL inducibility. The particular amino acid residues flanking to the present peptides may be composed of any kind of amino acids so long as they do not impair the CTL inducibility of the original peptide. Thus, the present invention encompasses peptides that include the modified peptides derived from MELK and have binding affinity to HLA antigens. Such peptides are typically less than about 40 amino acids, often less than about 20 amino acids, usually less than about 15 amino acids.

In general, the modification of one, two or more amino acids in a peptide will not influence the function of the peptide, and in some cases will even enhance the desired function of the original protein. In fact, modified peptides (i.e., peptides composed of an amino acid sequence in which one, two or several amino acid residues have been modified (i.e., substituted, deleted, added or inserted as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention may have both CTL inducibility and an amino acid sequence selected from among SEQ ID NOs: 35-45, wherein one, two or even more amino acids are added, inserted and/or substituted.

Those skilled in the art recognize that individual additions or substitutions to an amino acid sequence which alters a single amino acid or a small percentage of amino acids tend to result in the conservation of the properties of the original amino acid sequence. As such, they are often referred to as "conservative substitutions" or "conservative modifications", wherein the alteration of a protein results in a modified protein having a function analogous to the original protein. Conservative substitution tables providing functionally similar amino acids are well known in the art. Examples of amino acid side chain characteristics that are desirable to conserve include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, peptides of the present invention are not restricted thereto and can include non-conservative modifications, so long as the resulting modified peptide retains the CTL inducibility of the original peptide. Furthermore, modified peptides should not exclude CTL inducible peptides of polymorphic variants, interspecies homologues, and alleles of MELK.

Amino acid residues may be inserted, substituted or added to the peptides of the present invention or, alternatively, amino acid residues may be deleted therefrom to achieve a higher binding affinity. To retain the requisite CTL inducibility one preferably modifies modify (insert, delete, add and/or substitute) only a small number (for example, 1, 2 or several) or a small percentage of amino acids. Herein, the term "several" means 5 or fewer amino acids, for example, 4, 3 or fewer. The percentage of amino acids to be modified is preferably 20% or less, more preferably 15% or less, even more preferably 10% or less or 1 to 5%.

Moreover, peptides of the present invention can be inserted, substituted or added with amino acid residues or amino acid residues may be deleted to achieve a higher binding affinity. When used in the context of immunotherapy, the present peptides should be presented on the surface of a cell or exosome, preferably as a complex with an HLA antigen. In addition to peptides that are naturally displayed, since the regularity of the sequences of peptides displayed by binding to HLA antigens is already known (J Immunol 1994, 152: 3913; Immunogenetics 1995, 41: 178; J Immunol 1994, 155: 4307), modifications based on such regularity can be introduced into the immunogenic peptides of the invention. For example, it may be desirable to substitute the second amino acid from the N-terminus substituted with phenylalanine, tyrosine, methionine, or tryptophan, and/or the amino acid at the C-terminus with phenylalanine, leucine, isoleucine, tryptophan, or methionine in order to increase the HLA-A24 binding. Thus, peptides having the amino acid sequences selected from among SEQ ID NOs: 35-45 wherein the second amino acid from the N-terminus of the amino acid sequence of SEQ ID NOs is substituted with phenylalanine, tyrosine, methionine, or tryptophan, and peptides, and/or wherein the C-terminus of the amino acid sequence of the SEQ ID NOs is substituted with phenylalanine, leucine, isoleucine, tryptophan, or methionine are encompassed by the present invention.

Substitutions may be introduced not only at the terminal amino acids but also at the position of potential T cell receptor (TCR) recognition of peptides. Several studies have demonstrated that a peptide with amino acid substitutions may have equal to or better function than that of the original, for example, CAP1, p53 (264-272), Her-2/neu (369-377) or gp100 (209-217) (Zaremba et al. Cancer Res. 57, 4570-4577, 1997, T. K. Hoffmann et al. J Immunol. (2002) Feb. 1; 168 (3):1338-47, S. O. Dionne et al. Cancer Immunol immunother. (2003) 52: 199-206 and S. O. Dionne et al. Cancer Immunology, Immunotherapy (2004) 53, 307-314).

The present invention also contemplates the addition of one, two or several amino acids to the N and/or C-terminus of the described peptides. Such modified peptides having high HLA antigen binding affinity and retained CTL inducibility are also included in the present invention.

Note that, although the modification on the second amino acid from the N-terminus and the N and/or C-terminus of the peptides for achieving a higher binding affinity have been reported as above, the effect of the modification on the seventh amino acid from the N-terminus has not ever been elucidated.

However, when the peptide sequence is identical to a portion of the amino acid sequence of an endogenous or exogenous protein having a different function, side effects such as autoimmune disorders and/or allergic symptoms against specific substances may be induced. Therefore, it is preferable to first perform homology searches using available databases to avoid situations in which the sequence of the peptide matches the amino acid sequence of another protein. When it becomes clear from the homology searches that there exists not even a peptide with 1 or 2 amino acid differences as compared to the objective peptide, the objective peptide can be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce CTLs when presented on antigen-presenting cells (APCs). Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation with the peptides, mixing with CD8-positive cells, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependence on HLA class II restricted T(H) response) can be used. For example, the target cells can be radiolabeled with $^{51}Cr$ and such, and cytotoxic activity can be calculated from radioactivity released from the target cells. Alternatively, CTL inducibility can be assessed by measuring IFN-gamma produced and released by CTL in the presence of APCs that carry immobilized peptides, and visualizing the inhibition zone on the media using anti-IFN-gamma monoclonal antibodies.

As a result of examining the CTL inducibility of the peptides as described above, it was discovered that nonapeptides selected from among peptides having the amino acid sequences indicated by SEQ ID NOs: 35-45 showed particularly high CTL inducibility as well as high binding affinity to an HLA antigen. Thus, these peptides are exemplified as preferred embodiments of the present invention.

Furthermore, the result of homology analysis showed that those peptides do not have significant homology with peptides derived from any other known human gene products. This lowers the possibility of unknown or undesired immune responses arising when used for immunotherapy. Therefore, also from this aspect, these peptides are useful for eliciting immunity against MELK in cancer or endometriosis patients. Thus, the peptides of the present invention, preferably, peptides consisting of the amino acid sequence selected from among SEQ ID NOs: 35-45.

In addition to the above-described modifications, the peptides of the present invention may also be linked to other peptides, so long as the resulting linked peptide retains the requisite CTL inducibility of the original peptide. Examples of suitable other peptides include: the peptides of the present invention or the CTL inducible peptides derived from other TAAs. Suitable inter-peptide linkers are well known in the art, for example, AAY (P. M. Daftarian et al., J Trans Med 2007, 5:26), AAA, NKRK (R. P. M. Sutmuller et al., J Immunol. 2000, 165: 5 7308-7315) or K (S. Ota et al., Can Res. 62, 1471-1476, K. S. Kawamura et al., J Immunol. 2002, 168: 5709-5715).

For example, non-MELK tumor associated antigen peptides also can be used substantially simultaneously to increase the immune response via HLA class I and/or class II. It is well established that cancer cells can express more than one tumor associated gene. Thus, it is within the scope of routine experimentation for one of ordinary skill in the art to determine whether a particular subject expresses additional tumor associated genes, and then to include HLA class I and/or HLA class II binding peptides derived from expression products of such genes in MELK compositions or vaccines according to the present invention.

Examples of HLA class I and HLA class II binding peptides are known to one of ordinary skill in the art (for example, see Coulie, Stem Cells 13:393-403, 1995), and can be used in the present invention in a like manner as those disclosed herein. Thus, those of ordinary skill in the art can readily prepare polypeptides including one or more MELK peptides and one or more of the non-MELK peptides, or nucleic acids encoding such polypeptides, using standard procedures of molecular biology.

The above linked peptides are referred to herein as "polytopes", i.e., groups of two or more potentially immunogenic or immune response stimulating peptides which can be joined together in various arrangements (e.g., concatenated, overlapping). The polytope (or nucleic acid encoding the polytope) can be administered in a standard immunization protocol, e.g., to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., Proc. Natl. Acad. Sci USA 92(13):5845-5849, 1995; Gilbert et al., Nature Biotechnol. 15(12):1280-1284, 1997; Thomson et al., J Immunol. 157(2):822-826, 1996; Tam et al., J Exp. Med. 171(1):299-306, 1990). Polytopes containing various numbers and combinations of epitopes can be prepared and tested for recognition by CTLs and for efficacy in increasing an immune response.

In addition to the modification of the present peptides discussed above, the described peptides can be further linked to other substances, so long as they retain the CTL inducibility of the original peptide. Exemplary substances include: peptides, lipids, sugar and sugar chains, acetyl groups, natural and synthetic polymers, etc. The present peptides can contain modifications such as glycosylation, side chain oxidation, and/or phosphorylation; so long as the modifications do not destroy the biological activity of the original peptide. These kinds of modifications may confer additional functions (e.g., targeting function, and delivery function) and/or stabilize the peptides.

For example, to increase the in vivo stability of a polypeptide, it is known in the art to introduce D-amino acids, amino acid mimetics or unnatural amino acids; this concept can also be adopted to the present polypeptides. The stability of a polypeptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

Moreover, as noted above, among the modified peptides that are substituted, deleted or added by one, two or several amino acid residues, those having same or higher activity as compared to original peptides can be screened for or selected. The present invention, therefore, also provides the method of screening for or selecting modified peptides having same or higher activity as compared to originals. An illustrative method may include the steps of:

a: substituting, deleting or adding at least one amino acid residue of a peptide of the present invention, b: determining the activity of the peptide, and c: selecting the peptide having same or higher activity as compared to the original.

Herein, the activity to be assayed may include MHC binding activity, APC or CTL inducibility and cytotoxic activity.

Herein, the peptides of the present invention can also be described as "MELK peptide(s)" or "MELK polypeptide(s)".

III. PREPARATION OF THE MODIFIED MELK PEPTIDES

The peptides of the invention can be prepared using well known techniques. For example, the peptides can be prepared synthetically, using recombinant DNA technology or chemical synthesis. The peptides of the invention can be synthesized individually or as longer polypeptides composed of two or more peptides. The peptides can then be isolated, i.e., purified or isolated so as to be substantially free of other naturally occurring host cell proteins and fragments thereof, or any other chemical substances.

The peptides of the present invention may contain modifications, such as glycosylation, side chain oxidation, or phosphorylation provided such modifications do not destroy the biological activity of the original peptide. Other illustrative modifications include incorporation of D-amino acids or other amino acid mimetics that may be used, for example, to increase the serum half life of the peptides.

The peptides of the present invention may contain modifications, such as glycosylation, side chain oxidation, or phosphorylation; so long as the modifications do not destroy the biological activity of the peptides as described herein. Other modifications include incorporation of D-amino acids or other amino acid mimetics that can be used, for example, to increase the serum half life of the peptides.

A peptide of the present invention can be obtained through chemical synthesis based on the selected amino acid sequence. Examples of conventional peptide synthesis methods that can be adapted to the synthesis include, but are not limited to:

(i) Peptide Synthesis, Interscience, New York, 1966;

(ii) The Proteins, Vol. 2, Academic Press, New York, 1976;

(iii) Peptide Synthesis (in Japanese), Maruzen Co., 1975;

(iv) Basics and Experiment of Peptide Synthesis (in Japanese), Maruzen Co., 1985;

(v) Development of Pharmaceuticals (second volume) (in Japanese), Vol. 14 (peptide synthesis), Hirokawa, 1991;

(vi) WO99/67288; and (vii) Barany G. & Merrifield R. B., Peptides Vol. 2, "Solid Phase Peptide Synthesis", Academic Press, New York, 1980, 100-118.

Alternatively, the present peptides can be obtained adapting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide can also be produced in vitro adapting an in vitro translation system.

IV. POLYNUCLEOTIDES

The present invention also provides a polynucleotide which encodes any of the aforementioned peptides of the present invention. These include modified polynucleotides derived from the natural occurring MELK gene (GenBank Accession No. NM_014791 (SEQ ID NO: 46)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, and T is replaced by U in an RNA. One of skill will recognize that non-naturally occurring bases be included in polynucleotides, as well.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5.

V. EXOSOMES

The present invention further provides intracellular vesicles called exosomes, which present complexes formed between the peptides of this invention and HLA antigens on their surface. Exosomes can be prepared, for example, using the methods detailed in Japanese Patent Application Kohyo Publications Nos. Hei 11-510507 and WO99/03499, and can be prepared using APCs obtained from patients who are subject to treatment and/or prevention. The exosomes of this invention can be inoculated as vaccines, in a fashion similar to the peptides of this invention.

The type of HLA antigens contained in the complexes must match that of the subject requiring treatment and/or prevention. For example, in the Japanese population, HLA-A24 (particularly, A*2402) are prevalent and therefore would be appropriate for treatment of a Japanese patient. The use of the A24 type that is highly expressed among the Japanese and Caucasian is favorable for obtaining effective results. Typically, in the clinic, the type of HLA antigen of the patient requiring treatment is investigated in advance, which enables the appropriate selection of peptides having high levels of binding affinity to the particular antigen, or having CTL inducibility by antigen presentation. Furthermore, in order to obtain peptides having both high binding affinity and CTL inducibility, substitution, insertion and/or addition of 1, 2, or several amino acids can be performed based on the amino acid sequence of the modified MELK partial peptide, that is, modified peptides from MELK-A24-9-87_WT (SEQ ID NO: 6).

When using the A24 type HLA antigen for the exosome of the present invention, the peptides having a sequence of any one of SEQ ID NOs: 35-45 find use.

VI. ANTIGEN-PRESENTING CELLS (APCS)

The present invention also provides isolated APCs that present complexes formed between HLA antigens and the peptides of this invention on its surface. The APCs can be derived from patients who are subject to treatment and/or prevention, and can be administered as vaccines by themselves or in combination with other drugs including the peptides of this invention, exosomes, or CTLs.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DCs are a representative APC having the strongest CTL inducing action among APCs, DCs find use as the APCs of the present invention.

For example, the APCs of the present invention can be obtained by inducing DCs from peripheral blood monocytes and then contacting (stimulating) them with the peptides of this invention in vitro, ex vivo or in vivo. When the peptides of this invention are administered to the subjects, APCs that present the peptides of this invention are induced in the body of the subject. The phrase "inducing APC" includes contacting (stimulating) a cell with the peptides of the present invention, or nucleotides encoding the peptides of the present invention to present complexes formed between HLA antigens and the peptides of the present invention on cell's surface. Therefore, the APCs of this invention can be obtained by collecting the APCs from the subject after administering the peptides of this invention to the subject. Alternatively, the APCs of this invention can be obtained by contacting APCs collected from a subject with the peptide of this invention.

The APCs of the present invention can be administered alone or in combination with other drugs including the peptides, exosomes or CTLs of this invention to a subject for inducing immune response against cancer in the subject. For example, the ex vivo administration can include steps of:
a: collecting APCs from a first subject,
b: contacting the APCs of step a, with the peptide and
c: administering the APCs of step b to a second subject.

The first subject and the second subject can be the same individual, or may be different individuals. Alternatively, according to the present invention, use of the peptides of the present invention for manufacturing a pharmaceutical composition inducing antigen-presenting cells is provided. In addition, the present invention provides a method or process for manufacturing a pharmaceutical composition inducing antigen-presenting cells. Further, the present invention also provides the peptides of the present invention for inducing antigen-presenting cells. The APCs obtained by step b can be administered as a vaccine for treating and/or preventing endometriosis or cancer, examples of which include but are not limited to, breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC.

The present invention also provides a method or process for manufacturing a pharmaceutical composition for inducing APCs, wherein the method includes the step of admixing or formulating the peptide of the invention with a pharmaceutically acceptable carrier.

According to an aspect of the present invention, the APCs have a high level of CTL inducibility. In the term of "high level of CTL inducibility", the high level is relative to the level of that by APC contacting with no peptide or peptides which cannot induce the CTL. Such APCs having a high level of CTL inducibility can be prepared by a method which includes the step of transferring a polynucleotide encoding the peptide of this invention to APCs in vitro as well as the method mentioned above. The introduced genes can be in the form of DNAs or RNAs. Examples of methods for introduction include, without particular limitations, various methods conventionally performed in this field, such as lipofection, electroporation, and calcium phosphate method. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present peptides.

VII. CYTOTOXIC T LYMPHOCYTES (CTLS)

A CTL induced against any of the peptides of the present invention strengthens the immune response targeting cancer cells in vivo and thus can be used as vaccines in a fashion similar to the peptides per se. Thus, the present invention also provides isolated CTLs that are specifically induced or activated by any of the present peptides. Such CTLs can be obtained by (1) administering the peptide(s) of the present invention to a subject, collecting CTLs from the subject; or (2) contacting (stimulating) subject-derived APCs, and CD8-positive cells, or peripheral blood mononuclear leukocytes in vitro with the peptide(s) of the present invention and then isolating CTLs; or (3) contacting CD8-positive cells or peripheral blood mononuclear leukocytes in vitro with APCs or exosomes presenting a complex of an HLA antigen and the present peptide on its surface and then isolating CTLs; or (4) introducing a gene including a polynucleotide encoding a T cell receptor (TCR) subunit binding to the peptide of this invention to the CTLs. The aforementioned APCs and exosomes can be prepared by methods described above and the method of (4) is detailed bellow in section "VIII. T cell receptor (TCR)".

The CTLs of this invention can be derived from patients who are subject to treatment and/or prevention, and can be administered by themselves or in combination with other drugs including the peptides of this invention or exosomes for the purpose of regulating effects. The obtained CTLs act specifically against target cells presenting the peptides of this invention, for example, the same peptides used for induction. The target cells can be cells that endogenously express MELK, such as cancer or endometriosis cells, or cells that are transfected with the MELK gene; and cells that present a peptide of this invention on the cell surface due to stimulation by the peptide can also serve as targets of activated CTL attack.

VIII. T CELL RECEPTOR (TCR)

The present invention also provides a composition containing nucleic acids encoding polypeptides that are capable of forming a subunit of a T cell receptor (TCR), and methods of using the same. The TCR subunits have the ability to form TCRs that confer specificity to T cells against tumor cells expressing MELK. By using the known methods in the art, the nucleic acids of alpha- and beta-chains as the TCR subunits of the CTL induced with one or more peptides of this invention can be identified (WO2007/032255 and Morgan et al., J Immunol, 171, 3288 (2003)). For example, the PCR method is preferred to analyze the TCR. The PCR primers for the analysis can be, for example, 5'-R primers (5'-gtctaccag-gcattcgcttcat-3') as 5' side primers (SEQ ID NO: 49) and 3-TRa-C primers (5'-tcagctggaccacagccgcagcgt-3') specific to TCR alpha chain C region (SEQ ID NO: 50), 3-TRb-C1 primers (5'-tcagaaatcctttctcttgac-3') specific to TCR beta chain C1 region (SEQ ID NO: 51) or 3-TRbeta-C2 primers (5'-ctagcctctggaatcctttctctt-3') specific to TCR beta chain C2 region (SEQ ID NO: 52) as 3' side primers, but not limited. The derivative TCRs can bind target cells displaying the modified MELK peptide with high avidity, and optionally mediate efficient killing of target cells presenting the modified MELK peptide in vivo and in vitro.

The nucleic acids encoding the TCR subunits can be incorporated into suitable vectors, e.g., retroviral vectors. These vectors are well known in the art. The nucleic acids or the vectors containing them usefully can be transferred into a T cell, for example, a T cell from a patient. Advantageously, the invention provides an off-the-shelf composition allowing rapid modification of a patient's own T cells (or those of another mammal) to rapidly and easily produce modified T cells having excellent cancer cell killing properties.

The specific TCR is a receptor capable of specifically recognizing a complex of a peptide of the present invention and HLA molecule, giving a T cell specific activity against the target cell when the TCR on the surface of the T cell. A specific recognition of the above complex may be confirmed by any known methods, and preferred methods include, for example, tetramer analysis using HLA molecule and peptide of the invention, and ELISPOT assay. By performing the ELISPOT assay, it can be confirmed that a T cell expressing the TCR on the cell surface recognizes a cell by the TCR, and that the signal is transmitted intracellularly. The confirmation that the above-mentioned complex can give a T cell cytotoxic activity when the complex exists on the T cell surface may also be carried out by a known method. A preferred method includes, for example, the determination of cytotoxic activity against an HLA positive target cell, such as chromium release assay.

Also, the present invention provides CTLs which are prepared by transduction with the nucleic acids encoding the TCR subunits polypeptides that bind to the modified MELK peptide of, e.g., SEQ ID NOs: 35-45 in the context of HLA-A24. The transduced CTLs are capable of homing to cancer cells in vivo, and can be expanded by well known in vitro culturing methods (e.g., Kawakami et al., J Immunol., 142, 3452-3461 (1989)). The CTLs of the invention can be used to form an immunogenic composition useful in treating or the prevention of cancer in a patient in need of therapy or protection (WO2006/031221).

Prevention and prophylaxis include any activity which reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis include a wide range of prophylactic therapies aimed at alleviating the severity of the particular disorder, e.g., reducing the proliferation and metastasis of tumors or endometriosis, reducing angiogenesis.

Treating for the prophylaxis of cancer and/or the prevention of postoperative recurrence thereof may include one or more of the following steps, surgical removal of cancer cells, inhibition of the growth of cancerous cells, involution or regression of a tumor, induction of remission and suppression of occurrence of cancer, tumor regression, and reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

IX. PHARMACEUTICAL SUBSTANCES OR COMPOSITIONS

Since MELK expression is specifically elevated in endometriosis and cancers including breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC, as compared with normal tissue, the peptides of the present invention or polynucleotides encoding such peptides can be used for the treatment and/or for the prophylaxis of endometriosis and cancer or tumors, and/or prevention of postoperative recurrence thereof. Thus, the present invention provides a pharmaceutical substance or composition for treating and/or for the prophylaxis of cancer, tumor, or endometriosis and/or prevention of postoperative recurrence thereof, which includes one or more of the peptides of the present invention, or polynucleotides encoding the peptides as an active ingredient. Alternatively, the present peptides can be expressed on the surface of any of the foregoing exosomes or cells, such as APCs for the use as pharmaceutical substances or compositions. In addition, the aforementioned CTLs which target any of the peptides of the invention can also be used as the active ingredient of the present pharmaceutical substances or compositions.

The pharmaceutical compositions of the present invention can also find use as a vaccine. In the context of the present invention, the phrase "vaccine" (also referred to as an "immunogenic composition") refers to a substance that has the function to induce anti-tumor immunity upon inoculation into animals.

The pharmaceutical compositions of the present invention can be used to treat and/or prevent cancers or endometriosis, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

In another embodiment, the present invention also provides the use of an active ingredient in manufacturing a pharmaceutical composition or substance for treating cancer, tumor or endometriosis said active ingredient selected from among:
  (a) a peptide of the present invention;
  (b) a nucleic acid encoding such a peptide as disclosed herein in an expressible form;
  (c) an APC or an exosome presenting a peptide of the present invention on its surface; and
  (d) a cytotoxic T cell of the present invention.

Alternatively, the present invention further provides an active ingredient for use in treating or preventing cancer, tumor or endometriosis said active ingredient selected from among:
  (a) a peptide of the present invention;
  (b) a nucleic acid encoding such a peptide as disclosed herein in an expressible form;
  (c) an APC or an exosome presenting a peptide of the present invention on its surface; and
  (d) a cytotoxic T cell of the present invention.

Alternatively, the present invention further provides a method or process for manufacturing a pharmaceutical composition or substance for treating cancer, tumor or endometriosis wherein the method or process includes the step of formulating a pharmaceutically or physiologically acceptable carrier with an active ingredient selected from among:
  (a) a peptide of the present invention;
  (b) a nucleic acid encoding such a peptide as disclosed herein in an expressible form;
  (c) an APC or an exosome presenting a peptide of the present invention on its surface; and
  (d) a cytotoxic T cell of the present invention.

In another embodiment, the present invention also provides a method or process for manufacturing a pharmaceutical composition or substance for treating cancer, tumor or endometriosis wherein the method or process includes the steps of admixing an active ingredient with a pharmaceutically or physiologically acceptable carrier, wherein the active ingredient is selected from among:
  (a) a peptide of the present invention;
  (b) a nucleic acid encoding such a peptide as disclosed herein in an expressible form;

(c) an APC or an exosome presenting a peptide of the present invention on its surface; and (d) a cytotoxic T cell of the present invention.

Alternatively, the present invention also provides a substance for inducing CTL, wherein the substance consists of one or more peptide(s) of the present invention, or one or more polynucleotide(s) of the present invention.

Alternatively, the pharmaceutical composition or substance or the present invention may be used for either or both the prophylaxis of cancer, tumor or endometriosis and prevention of postoperative recurrence thereof.

The present pharmaceutical substances or compositions find use as a vaccine. As noted above, in the context of the present invention, the phrase "vaccine" (also referred to as an "immunogenic composition") refers to a substance that has the function to induce anti-tumor immunity upon inoculation into animals.

The pharmaceutical substances or compositions of the present invention can be used to treat and/or prevent cancers, tumors or endometriosis and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

According to the present invention, peptides having an amino acid sequence of any one of SEQ ID NOs: 35-45 have been found to be HLA-A24 restricted epitope peptides or candidates that can induce potent and specific immune response. Therefore, the present pharmaceutical substances or compositions which include any of these peptides having the amino acid sequences of SEQ ID NOs: 35-45 are particularly suited for the administration to subjects whose HLA antigen is HLA-A24. The same applies to pharmaceutical substances and compositions which include polynucleotides encoding any of these peptides (i.e., the polynucleotides of this invention).

Cancers, tumors, or endometriosis to be treated by the pharmaceutical substances or compositions of the present invention are not limited and include all kinds of diseases wherein MELK is involved, including but not limited to, endometriosis, breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC.

The present pharmaceutical substances or compositions can contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical substances or compositions of the present invention can optionally include other therapeutic substances as an active ingredient, so long as the substance does not inhibit the antitumoral effect of the active ingredient, e.g., any of the present peptides. For example, formulations can include anti-inflammatory substances, pain killers, chemotherapeutics, and the like. In addition to including other therapeutic substances in the medicament itself, the medicaments of the present invention can also be administered sequentially or concurrently with the one or more other pharmacologic substances. The amounts of medicament and pharmacologic substance depend, for example, on what type of pharmacologic substance(s) is/are used, the disease being treated, and the scheduling and routes of administration. It should be understood that in addition to the ingredients particularly mentioned herein, the pharmaceutical substances or compositions of this invention can include other substances conventional in the art having regard to the type of formulation in question.

In one embodiment of the present invention, the present pharmaceutical substances or compositions can be included in articles of manufacture and kits containing materials useful for treating the pathological conditions of the disease to be treated, e.g., cancer, or endometriosis. The article of manufacture can include a container of any of the present pharmaceutical substances or compositions with a label. Suitable containers include bottles, vials, and test tubes. The containers can be formed from a variety of materials, such as glass or plastic. The label on the container should indicate the substance is used for treating or prevention of one or more conditions of the disease. The label can also indicate directions for administration and so on.

In addition to the container described above, a kit including a pharmaceutical substance or composition of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical substances or compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Substances or Compositions Containing the Peptides as the Active Ingredient The peptides of this invention can be administered directly as a pharmaceutical substance or composition, or if necessary, may be formulated by conventional formulation methods. In the latter case, in addition to the peptides of this invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical substances or compositions can contain as necessary, stabilizers, suspensions, preservatives, surfactants and such. The pharmaceutical substances or compositions of this invention can be used for anticancer purposes.

The peptides of this invention can be prepared as a combination composed of two or more of the peptides of the present invention, to induce CTLs in vivo. The peptide combination can take the form of a cocktail or can be conjugated to each other using standard techniques. For example, the peptides can be chemically linked or expressed as a single fusion polypeptide sequence. The peptides in the combination can be the same or different. By administering the peptides of this invention, the peptides are presented at a high density by the HLA antigens on APCs, then CTLs that specifically react toward the complex formed between the displayed peptide and the HLA antigen are induced. Alternatively, APCs (e.g., DCs) are removed from subjects and then stimulated by the peptides of the present invention to obtain APCs that present any of the peptides of this invention on their cell surface. These APCs are readministered to the subjects to induce CTLs in the subjects, and as a result, aggressiveness towards the tumor-associated endothelium can be increased.

The pharmaceutical substances or compositions for the treatment and/or prevention of cancer, tumor or endometriosis which include a peptide of this invention as the active ingredient, can also include an adjuvant known to effectively induce cellular immunity. Alternatively, the pharmaceutical substances or compositions can be administered with other active ingredients or administered by formulation into granules. An adjuvant refers to a compound that enhances the immune response against the protein when administered together (or successively) with the protein having immunological activity. Adjuvants contemplated herein include those described in the literature (Clin Microbiol Rev 1994, 7: 277-89). Examples of suitable adjuvants include aluminum phosphate, aluminum hydroxide, alum, cholera toxin, *salmonella* toxin, may be, but are not limited thereto.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Preferable examples of the salts include salts with an alkali metal, salts with a metal, salts with an organic base, salts with an organic acid and salts with an inorganic acid. As used herein, "pharmaceutically acceptable salt" refers to those salts which retain the biological effectiveness and properties of the compound and which are obtained by reaction with inorganic acids or bases such as hydrochloric acid, hydrobromic acid, sulfuric acid, nitric acid, phosphoric acid, methanesulfonic acid, ethanesulfonic acid, p-toluenesulfonic acid, salicylic acid and the like.

In some embodiments, the pharmaceutical substances or compositions of the present invention may further include a component which primes CTLs. Lipids have been identified as substances capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinyl-seryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of this invention can be adjusted appropriately according to the disease to be treated, age of the patient, weight, method of administration, and such, and is ordinarily 0.001 mg to 1000 mg, for example, 0.1 mg to 10 mg, and can be administered once in a few days to few months. One skilled in the art can appropriately select a suitable dose.

(2) Pharmaceutical Substances or Compositions Containing Polynucleotides as the Active Ingredient The pharmaceutical substances or compositions of the present invention can also contain nucleic acids encoding the peptides disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a subject can be either direct, in which case the subject is directly exposed to a polynucleotide-carrying vector, or indirect, in which case, cells are first transformed with the polynucleotide of interest in vitro, then the cells are transplanted into the subject. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of this invention can be adjusted appropriately according to the disease to be treated, age of the patient, weight, method of administration, and such, and is ordinarily 0.001 mg to 1000 mg, for example, 0.1 mg to 10 mg, and can be administered once every a few days to once every few months. One skilled in the art can appropriately select the suitable dose.

X. METHODS USING THE PEPTIDES, EXOSOMES, APCS AND CTLS

The peptides and polynucleotides of the present invention can be used for inducing APCs and CTLs. The exosomes and APCs of the present invention can be also used for inducing CTLs. The peptides, polynucleotides, exosomes and APCs can be used in combination with any other compounds so long as the additional compounds do not inhibit CTL inducibility. Thus, any of the aforementioned pharmaceutical substances or compositions of the present invention can be used for inducing CTLs. In addition thereto, those including the peptides and polynucleotides can also be used for inducing APCs as discussed explained below.

(1) Method of Inducing Antigen-Presenting Cells (APCs)

The present invention provides methods of inducing APCs with high CTL inducibility using the peptides or polynucleotides of this invention.

The methods of the present invention include the step of contacting APCs with the peptides of this invention in vitro, ex vivo or in vivo. For example, the method contacting APCs with the peptides ex vivo can include the steps of:
  a: collecting APCs from a subject, and
  b: contacting the APCs of step a with the peptide.

The APCs are not limited to a particular kind of cells and include DCs, Langerhans cells, macrophages, B cells, and activated T cells, which are known to present proteinaceous antigens on their cell surface so as to be recognized by lymphocytes. DCs can be preferably used due to its strongest CTL inducibility among the APCs. Any peptides of the present invention can be used as the peptide of step b by themselves or in combination with other peptides of this invention.

Alternatively, the peptides of the present invention may be administered to a subject to contact the peptides with APCs in vivo. Consequently, APCs with high CTL inducibility can be induced in the body of the subject. Thus, the present invention also contemplates a method of administering the peptides of this invention to a subject to induce APCs in vivo. It is also possible to administer polynucleotides encoding the peptides of this invention to a subject in an expressible form, so that the peptides of this invention are expressed and contacted with APCs in vivo, to consequently induce APCs with high CTL inducibility in the body of the subject. Thus, the present invention also contemplates a method of administering the polynucleotides of this invention to a subject to induce APCs in vivo. The phrase "expressible form" is defined above in section "IX. Pharmaceutical substances (2) Pharmaceutical substances containing polynucleotides as the active ingredient".

Furthermore, the present invention includes introducing the polynucleotide of this invention into an APC to induce APCs with CTL inducibility. For example, the method may include the steps of:
  a: collecting APCs from a subject, and
  b: introducing a polynucleotide encoding a peptide of this invention.

Step b can be performed as described above in section "VI. Antigen-presenting cells".

Alternatively, the present invention provides a method for preparing an antigen-presenting cell (APC) which specifically induces CTL activity against MELK, wherein the method can include one of the following steps:
  a: contacting an APC with a peptide of the present invention in vitro, ex vivo or in vivo; and
  b: introducing a polynucleotide encoding a peptide of the present invention into an APC.

(2) Method of Inducing CTLs

The present invention also provides methods for inducing CTLs using the peptides, polynucleotides, or exosomes or APCs of this invention.

The present invention also provides methods for inducing CTLs using a polynucleotide encoding a polypeptide that is capable of forming a T cell receptor (TCR) subunit recognizing a complex of the peptides of the present invention and HLA antigens. Preferably, the methods for inducing CTLs include at least one step selected from among:
  a: contacting a CD8-positive T cell with an antigen-presenting cell and/or an exosome that presents on its surface a complex of an HLA antigen and a peptide of the preset invention; and
  b: introducing a polynucleotide encoding a polypeptide that is capable of forming a TCR subunit recognizing a complex of a peptide of the present invention and an HLA antigen into a CD8 positive cell.

When the peptides, the polynucleotides, APCs, or exosomes of the present invention are administered to a subject, CTLs are induced in the body of the subject, and the strength of the immune response targeting the cancer cells is enhanced. Thus, the present invention also contemplates a method which includes the step of administering the peptides, the polynucleotides, the APCs or exosomes of this invention to a subject to induce CTLs.

Alternatively, CTLs can be also induced by their ex vivo use. In such case, after the induction of CTLs, the activated CTLs would be returned to the subject. For example, a method of the present invention to induce CTLs can include steps of:
  a: collecting APCs from a subject;
  b: contacting the APCs of step a) with the peptide; and
  c: co-culturing the APCs of step b with CD8-positive cells.

The APCs to be co-cultured with the CD8-positive cells in above step c can also be prepared by transferring a gene that includes a polynucleotide of this invention into APCs as described above in section "VI. Antigen-presenting cells"; but are not limited thereto and any APCs which effectively presents on its surface a complex of an HLA antigen and the peptide of this invention can be used for the instant method.

Instead of such APCs, the exosomes that presents on its surface a complex of an HLA antigen and the peptide of this invention can be also used. Namely, the present invention also contemplates a method wherein exosomes presenting on its surface a complex of an HLA antigen and the peptide of this invention are co-cultured with CD8-positive cells. Such exosomes may be prepared by the methods described above in section "V. Exosomes".

Furthermore, CTL can be induced by introducing a gene that includes a polynucleotide encoding the TCR subunit binding to the peptide of this invention into CD8-positive cells. Such transduction can be performed as described above in section "VIII. T cell receptor (TCR)".

In addition, the present invention provides a method or process for manufacturing a pharmaceutical substance or composition inducing CTLs, wherein the method includes the step of admixing or formulating the peptide of the present invention with a pharmaceutically acceptable carrier.

(3) Method of Inducing Immune Response

Moreover, the present invention provides methods for an inducing immune response against diseases related to MELK. Suitable disease include endometriosis and cancer, examples of which include, but are not limited to, breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC.

The methods include the step of administering substances or compositions containing any of the peptides of the present invention or polynucleotides encoding them. The present inventive method also contemplates the administration of exosomes or APCs presenting any of the peptides of the present invention. For details, see the item of "IX. Pharmaceutical substances or compositions", particularly the part describing the use of the pharmaceutical substances and compositions of the present invention as vaccines. In addition, the exosomes and APCs that can be employed for the present methods for inducing immune response are described in detail under the items of "V. Exosomes", "VI. Antigen-presenting cells (APCs)", and (1) and (2) of "X. Methods using the peptides, exosomes, APCs and CTLs", supra.

The present invention also provides a method or process for manufacturing a pharmaceutical substance or composition inducing immune response, wherein the method includes the step of admixing or formulating the peptide of the present invention with a pharmaceutically acceptable carrier.

The methods include the administration of a vaccine of the present invention, which contains:
a: one or more epitope peptides of the present invention, or an immunologically active fragment thereof;
b: one or more polynucleotides encoding the epitope peptides or the immunologically active fragment of (a);
c: one or more isolated CTLs of the present invention; or
d: one or more isolated antigen-presenting cells of the present invention.

In the context of the present invention, diseases overexpressing MELK can be treated with these active ingredients. The diseases include, but are not limited to, endometriosis, breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC. Accordingly, prior to the administration of the vaccines or pharmaceutical compositions containing the active ingredients, it is preferable to confirm whether the expression level of MELK in the cancer or endometriosis cells or tissues to be treated is enhanced compared with normal cells of the same organ. Thus, in one embodiment, the present invention provides a method for treating cancer or endometriosis (over)expressing MELK, which method may include the steps of:
  i) determining the expression level of MELK in cancer or endometriosis cells or tissue(s) obtained from a subject with the cancer to be treated;
  ii) comparing the expression level of MELK with normal control; and
  iii) administrating at least one component selected from the group consisting of (a) to (d) described above to a subject with cancer or endometriosis overexpressing MELK compared with normal control. Alternatively, the present invention also provides a vaccine or pharmaceutical composition containing at least one component selected from the group consisting of (a) to (d) described above, for use in administrating to a subject having cancer or endometriosis overexpressing MELK. In other words, the present invention further provides a method for identifying a subject to be treated with the MELK polypeptide of the present invention, which method may include the step of determining an expression level of MELK in subject-derived cancer or endometriosis cells or tissue(s), wherein an increase of the level compared to a normal control level of the gene indicates that the subject has cancer or endometriosis which may be treated with the MELK polypeptide of the present invention. The method of treating cancer or endometriosis of the present invention will be described in more detail below.

A subject to be treated by the present method is preferably a mammal. Exemplary mammals include, but are not limited to, e.g., human, non-human primate, mouse, rat, dog, cat, horse, and cow.

According to the present invention, the expression level of MELK in cancer or endometriosis cells or tissues obtained from a subject is determined. The expression level can be determined at the transcription product level, using methods known in the art. For example, the mRNA of MELK may be quantified using probes by hybridization methods (e.g., Northern hybridization). The detection may be carried out on a chip or an array. The use of an array is preferable for detecting the expression level of MELK. Those skilled in the art can prepare such probes utilizing the sequence information of MELK. For example, the cDNA of MELK may be used as the probes. If necessary, the probes may be labeled with a suitable label, such as dyes, fluorescent substances and isotopes, and the expression level of the gene may be detected as the intensity of the hybridized labels.

Furthermore, the transcription product of MELK (e.g., SEQ ID NO: 46) may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of MELK. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degree Centigrade lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degree Centigrade for short probes or primers (e.g., 10 to 50 nucleotides) and at least about 60 degree Centigrade for longer probes or primers. Stringent conditions may also be achieved with the addition of destabilizing substances, such as formamide.

The probes or primers may be of specific sizes. The sizes may range from at least 10 nucleotides, at least 12 nucleotides, at least 15 nucleotides, at least 20 nucleotides, at least 25 nucleotides, at least 30 nucleotides and the probes and primers may range in size from 5-10 nucleotides, 10-15 nucleotides, 15-20 nucleotides, 20-25 nucleotides and 25-30 nucleotides.

Alternatively, the translation product may be detected for the diagnosis of the present invention. For example, the quantity of MELK protein (SEQ ID NO: 47) may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')2, Fv, etc.) of the antibody may be used for the detection, so long as the fragment or modified antibody retains the binding ability to the MELK protein. Methods to prepare these kinds of antibodies for the detection of proteins are well known in the art, and any method may be employed in the present invention to prepare such antibodies and equivalents thereof. As another method to detect the expression level of MELK gene based on its translation product, the intensity of staining may be measured via immunohistochemical analysis using an antibody against the MELK protein. Namely, in this measurement, strong staining indicates increased presence/level of the protein and, at the same time, high expression level of MELK gene.

The expression level of a target gene, e.g., the MELK gene, in cancer or endometriosis cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time with the cancer or endometriosis cells by using a sample(s) previously collected and stored from a subject/subjects whose disease state(s) (diseased or non-diseased) is/are known. In addition, normal cells obtained from non-diseased regions of an organ that has the cancer or endometriosis to be treated may be used as normal control. Alternatively, the control level may be determined by a statistical method based on the results obtained by analyzing previously determined expression level(s) of MELK gene in samples from subjects whose disease states are known. Furthermore, the control level can be derived from a database of expression patterns from previously tested cells. Moreover, according to an aspect of the present invention, the expression level of MELK gene in a biological sample may be compared to multiple control levels, which are determined from multiple reference samples. It is preferred to use a control level determined from a reference sample derived from a tissue type similar to that of the subject-derived biological sample. Moreover, it is preferred to use the standard value of the expression levels of MELK gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-diseased is referred to as a "normal control level". On the other hand, if the control level is determined from a diseased biological sample, it is referred to as a "diseased control level".

When the expression level of MELK gene is increased as compared to the normal control level, or is similar/equivalent to the diseased control level, the subject may be diagnosed with diseased to be treated.

More specifically, the present invention provides a method of (i) diagnosing whether a subject has the cancer or endometriosis to be treated, and/or (ii) selecting a subject for cancer or endometriosis treatment, which method includes the steps of:
 a: determining the expression level of MELK in cancer or endometriosis cells or tissue(s) obtained from a subject who is suspected to have the cancer or endometriosis to be treated;
 b: comparing the expression level of MELK with a normal control level;
 c: diagnosing the subject as having the cancer or endometriosis to be treated, if the expression level of MELK is increased as compared to the normal control level; and
 d: selecting the subject for cancer or endometriosis treatment, if the subject is diagnosed as having the cancer or endometriosis to be treated, in step (c).

Alternatively, such a method includes the steps of:
 a: determining the expression level of MELK in cancer or endometriosis cells or tissue(s) obtained from a subject who is suspected to have the cancer or endometriosis to be treated;
 b: comparing the expression level of MELK with a diseased control level;
 c: diagnosing the subject as having the cancer or endometriosis to be treated, if the expression level of MELK is similar or equivalent to the diseased control level; and
 d: selecting the subject for cancer or endometriosis treatment, if the subject is diagnosed as having the cancer or endometriosis to be treated, in step (c).

The present invention also provides a kit for determining a subject suffering from endometriosis or cancer that can be treated with the MELK polypeptide of the present invention, which may also be useful in assessing and/or monitoring the efficacy of a cancer immunotherapy. Preferably, the cancer includes, but is not limited to, breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC. More particularly, the kit preferably includes at least one reagent for detecting the expression of the MELK gene in a subject-derived cancer or endometriosis cell, which reagent may be selected from the group of:
 (a) a reagent for detecting mRNA of the MELK gene;
 (b) a reagent for detecting the MELK protein; and
 (c) a reagent for detecting the biological activity of the MELK protein.

Suitable reagents for detecting mRNA of the MELK gene include nucleic acids that specifically bind to or identify the MELK mRNA, such as oligonucleotides which have a complementary sequence to a portion of the MELK mRNA. These kinds of oligonucleotides are exemplified by primers and probes that are specific to the MELK mRNA. These kinds of oligonucleotides may be prepared based on methods well known in the art. If needed, the reagent for detecting the MELK mRNA may be immobilized on a solid matrix. Moreover, more than one reagent for detecting the MELK mRNA may be included in the kit.

On the other hand, suitable reagents for detecting the MELK protein include antibodies to the MELK protein. The antibody may be monoclonal or polyclonal. Furthermore, any fragment or modification (e.g., chimeric antibody, scFv, Fab, F(ab')2, Fv, etc.) of the antibody may be used as the reagent, so long as the fragment or modified antibody retains the binding ability to the MELK protein. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the MELK protein may be included in the kit.

The kit may contain more than one of the aforementioned reagents. For example, tissue samples obtained from subjects without cancer or endometriosis, or suffering from cancer or endometriosis, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers include bottles, vials, and test tubes. The containers may be formed from a variety of materials, such as glass or plastic.

In an embodiment of the present invention, when the reagent is a probe against the MELK mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of MELK mRNA present in the sample. The detection sites may be configured in any suitably detectable shape and are typically in the shape of a bar or dot spanning the width of a test strip.

The kit of the present invention may further include a positive control sample or MELK standard sample. The positive control sample of the present invention may be prepared by collecting MELK positive samples and then assaying their MELK levels. Alternatively, a purified MELK protein or polynucleotide may be added to cells that do not express MELK to form the positive sample or the MELK standard sample. In the present invention, purified MELK may be a recombinant protein. The MELK level of the positive control sample is, for example, more than the cut off value.

In one embodiment, the present invention further provides a diagnostic kit including, a protein or a partial protein thereof capable of specifically recognizing the antibody of the present invention or the fragment thereof.

Examples of the partial peptide of the protein of the present invention include polypeptides composed of at least 8, preferably 15, and more preferably 20 contiguous amino acids in the amino acid sequence of the protein of the present invention. Cancer or endometriosis can be diagnosed by detecting an antibody in a sample (e.g., blood, tissue) using a protein or a peptide (polypeptide) of the present invention. The method for preparing the protein of the present invention and peptides are as described above.

The methods for diagnosing cancer or endometriosis of the present invention can be performed by determining the difference between the amount of anti-MELK antibody and that in the corresponding control sample as describe above. The subject is suspected to be suffering from cancer or endometriosis, if cells or tissues of the subject contain antibodies against the expression products (MELK) of the gene and the quantity of the anti-MELK antibody is determined to be more than the cut off value in level compared to that in normal control.

In another embodiment, a diagnostic kit of the present invention may include the peptide of the present invention and an HLA molecule binding thereto. The method for detecting antigen specific CTLs using antigenic peptides and HLA molecules has already been established (for example, Altman J D et al., Science. 1996, 274(5284): 94-6). Thus, the complex of the peptide of the present invention and the HLA molecule can be applied to the detection method to detect tumor antigen specific CTLs, thereby enabling earlier detection, recurrence and/or metastasis of cancer. Further, it can be employed for the selection of subjects applicable with the pharmaceuticals including the peptide of the present invention as an active ingredient, or the assessment of the treatment effect of the pharmaceuticals.

Particularly, according to the known method (see, for example, Altman J D et al., Science. 1996, 274(5284): 94-6), the oligomer complex, such as tetramer, of the radiolabeled HLA molecule and the peptide of the present invention can be prepared. With using the complex, the diagnosis can be done, for example, by quantifying the antigen-peptide specific CTLs in the peripheral blood lymphocytes derived from the subject suspected to be suffering from cancer.

The present invention further provides a method or diagnostic agents for evaluating immunological response of subject by using peptide epitopes as described herein. In one embodiment of the invention, HLA restricted peptides as described herein may be used as reagents for evaluating or predicting an immune response of a subject. The immune response to be evaluated may be induced by contacting an immunogen with immunocompetent cells in vitro or in vivo. In preferred embodiments, the immunocompetent cells for evaluating an immunological response, may be selected from among peripheral blood, peripheral blood lymphocyte (PBL), and peripheral blood mononuclear cell (PBMC). Methods for collecting or isolating such immunocompetent cells are well known in the arts. In some embodiments, any substances or compositions that may result in the production of antigen specific CTLs that recognize and bind to the peptide epitope(s) may be employed as the reagent. The peptide reagents may need not to be used as the immunogen. Assay systems that are used for such an analysis include relatively recent technical developments such as tetramers, staining for intracellular lymphokines and interferon release assays, or ELISPOT assays. In a preferred embodiment, immunocompetent cells to be contacted with peptide reagent may be antigen presenting cells including dendritic cells.

For example, peptides of the present invention may be used in tetramer staining assays to assess peripheral blood mononuclear cells for the presence of antigen-specific CTLs following exposure to a tumor cell antigen or an immunogen. The HLA tetrameric complex may be used to directly visualize antigen specific CTLs (see, e.g., Ogg et al., Science 279: 2103-2106, 1998; and Altman et al, Science 174: 94-96, 1996) and determine the frequency of the antigen-specific CTL population in a sample of peripheral blood mononuclear cells. A tetramer reagent using a peptide of the invention may be generated as described below.

A peptide that binds to an HLA molecule is refolded in the presence of the corresponding HLA heavy chain and beta 2-microglobulin to generate a trimolecular complex. In the complex, carboxyl terminal of the heavy chain is biotinylated at a site that was previously engineered into the protein. Then, streptavidin is added to the complex to form tetramer composed of the trimolecular complex and streptavidin. By means of fluorescently labeled streptavidin, the tetramer can be used to stain antigen specific cells. The cells can then be identified, for example, by flow cytometry. Such an analysis may be used for diagnostic or prognostic purposes. Cells identified by the procedure can also be used for therapeutic purposes.

The present invention also provides reagents to evaluate immune recall responses (see, e.g., Bertoni et al, J. Clin. Invest. 100: 503-513, 1997 and Penna et al., J Exp. Med. 174: 1565-1570, 1991) including peptides of the present invention. For example, patient PBMC samples from individuals with cancer to be treated can be analyzed for the presence of antigen-specific CTLs using specific peptides. A blood sample containing mononuclear cells can be evaluated by cultivating the PBMCs and stimulating the cells with a peptide of the invention. After an appropriate cultivation period, the expanded cell population can be analyzed, for example, for CTL activity.

The peptides may also be used as reagents to evaluate the efficacy of a vaccine. PBMCs obtained from a patient vaccinated with an immunogen may be analyzed using, for example, either of the methods described above. The patient is HLA typed, and peptide epitope reagents that recognize the allele specific molecules present in the patient are selected for the analysis. The immunogenicity of the vaccine may be indicated by the presence of epitope-specific CTLs in the PBMC sample. The peptides of the invention may also be used to make antibodies, using techniques well known in the art (see, e.g., CURRENT PROTOCOLS IN IMMUNOLOGY, Wiley/Greene, NY; and Antibodies A Laboratory Manual, Harlow and Lane, Cold Spring Harbor Laboratory Press, 1989), which may find use as reagents to diagnose, detect or monitor cancer or endometriosis. Such antibodies may include those that recognize a peptide in the context of an HLA molecule, i.e., antibodies that bind to a peptide-MHC complex.

The peptides and compositions of the present invention have a number of additional uses, some of which are described herein. For instance, the present invention provides a method for diagnosing or detecting a disorder characterized by expression of a MELK immunogenic polypeptide. These methods involve determining expression of a MELK HLA binding peptide, or a complex of a MELK HLA binding peptide and an HLA class I molecule in a biological sample. The expression of a peptide or complex of peptide and HLA class I molecule can be determined or detected by assaying with a binding partner for the peptide or complex. In a preferred embodiment, a binding partner for the peptide or complex may be an antibody recognizes and specifically bind to the peptide. The expression of MELK in a biological sample, such as a tumor or endometriosis biopsy, can also be tested by standard PCR amplification protocols using MELK primers. An example of tumor expression is presented herein and further disclosure of exemplary conditions and primers for MELK amplification can be found in WO2003/27322.

Preferably, the diagnostic methods involve contacting a biological sample isolated from a subject with an agent specific for the MELK HLA binding peptide to detect the presence of the MELK HLA binding peptide in the biological sample. As used herein, "contacting" means placing the biological sample in sufficient proximity to the agent and under the appropriate conditions of, e.g., concentration, temperature, time, ionic strength, to allow the specific interaction between the agent and MELK HLA binding peptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al.

The diagnostic method of the present invention can be performed in either or both of in vivo and in vitro. Accordingly, biological sample can be located in vivo or in vitro in the present invention. For example, the biological sample can be a tissue in vivo and the agent specific for the MELK immunogenic polypeptide can be used to detect the presence of such molecules in the tissue. Alternatively, the biological sample can be collected or isolated in vitro (e.g., a blood sample, tumor biopsy, tissue extract). In a particularly preferred embodiment, the biological sample can be a cell-containing sample, more preferably a sample containing tumor or endometriosis cells collected from a subject to be diagnosed or treated.

Alternatively, the diagnosis can be done, by a method which allows direct quantification of antigen-specific T cells by staining with Fluorescein-labeled HLA multimeric complexes (e.g., Altman, J. D. et al., 1996, Science 274: 94; Altman, J. D. et al., 1993, Proc. Natl. Acad. Sci. USA 90: 10330). Staining for intracellular lymphokines, and interferon-gamma release assays or ELISPOT assays also has been provided. Multimer staining, intracellular lymphokine staining and ELISPOT assays all appear to be at least 10-fold more sensitive than more conventional assays (Murali-Krishna, K. et al., 1998, Immunity 8: 177; Lalvani, A. et al., 1997, J. Exp. Med. 186: 859; Dunbar, P. R. et al., 1998, Curr. Biol. 8: 413). Pentamers (e.g., US 2004-209295A), dextramers (e.g., WO 02/072631), and streptamers (e.g., Nature medicine 6. 631-637 (2002)) may also be used.

For instance, in some embodiments, the present invention provides a method for diagnosing or evaluating an immunological response of a subject administered at least one of MELK peptides of the present invention, the method including the steps of:

a: contacting an immunogen with immunocompetent cells under the condition suitable of induction of CTL specific to the immunogen;

b: detecting or determining induction level of the CTL induced in step (a); and c: correlating the immunological response of the subject with the CTL induction level.

In the present invention, the immunogen is at least one of (a) a MELK peptide selected from among the amino acid sequences of SEQ ID NOs: 6, 35-45, peptides having such amino acid sequences, and peptides having in which such amino acid sequences have been modified with 1, 2 or more amino acid substitution(s). In the meantime, conditions suitable of induction of immunogen specific CTL are well known in the art. For example, immunocompetent cells may be cultured in vitro under the presence of immunogen(s) to induce immunogen specific CTL. In order to induce immunogen specific CTLs, any stimulating factors may be added to the cell culture. For example, IL-2 is preferable stimulating factors for the CTL induction.

In some embodiments, the step of monitoring or evaluating immunological response of a subject to be treated with peptide cancer therapy may be performed before, during and/or after the treatment. In general, during a protocol of cancer therapy, immunogenic peptides are administered repeatedly to a subject to be treated. For example, immunogenic peptides may be administered every week for 3-10 weeks. Accordingly, the immunological response of the subject can be evaluated or monitored during the cancer therapy protocol.

Alternatively, the step of evaluation or monitoring of immunological response to the cancer therapy may at the completion of the therapy protocol.

According to the present invention, enhanced induction of immunogen specific CTL as compared with a control indicates that the subject to be evaluated or diagnosed immunologically responded to the immunogen(s) which have been administered. Suitable controls for evaluating the immunological response may include, for example, a CTL induction level when the immunocompetent cells are contacted with no peptide, or control peptide(s) having amino acid sequences other than any MELK peptides. (e.g. random amino acid sequence).

In a preferred embodiment, the immunological response of the subject is evaluated in a sequence specific manner, by comparison with an immunological response between each immunogen administered to the subject. In particular, even when a mixture of some kinds of MELK peptides is administered to the subject, immunological response might vary depending on the peptides. In that case, by comparison of the immunological response between each peptide, peptides to which the subject show higher response can be identified.

XI. ANTIBODIES

The present invention further provides antibodies that bind to the peptide of the present invention. Preferred antibodies specifically bind to the peptide of the present invention and will not bind (or will bind weakly) to non-peptide of the present invention. Alternatively, antibodies bind to the peptide of the invention as well as the homologs thereof. Antibodies against the peptide of the invention can find use in cancer or endometriosis diagnostic and prognostic assays, and imaging methodologies. Similarly, such antibodies can find use in the treatment, diagnosis, and/or prognosis of other cancers or endometriosis, to the extent MELK is also expressed or overexpressed in cancer or endometriosis patient. Moreover, intracellularly expressed antibodies (e.g., single chain antibodies) may find therapeutic use in treating endometriosis or cancers in which the expression of MELK is involved, examples of which include, but are not limited to, breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC.

The present invention also provides various immunological assay for the detection and/or quantification of the MELK protein (SEQ ID NO: 47) or fragments thereof polypeptides having an amino acid sequences selected from among SEQ ID NOs: 35, 41, 44. Such assays may include one or more anti-MELK antibodies capable of recognizing and binding a MELK protein or fragments thereof, as appropriate. In the context of the present invention, anti-MELK antibodies binding to MELK polypeptide preferably recognize a polypeptide having an amino acid sequences selected from among SEQ ID NOs: 35, 41, 44. A binding specificity of antibody can be confirmed with inhibition test. That is, when the binding between an antibody to be analyzed and full-length of MELK polypeptide is inhibited under presence of any fragment polypeptides having an amino acid sequence selected from among SEQ ID NOs: 35, 41, 44, it is shown that this antibody specifically binds to the fragment. In the context of the present invention, such immunological assays are performed within various immunological assay formats well known in the art, including but not limited to, various types of radioimmunoassays, immuno-chromatograph technique, enzyme-linked immunosorbent assays (ELISA), enzyme-linked immunofluorescent assays (ELIFA), and the like.

Related immunological but non-antibody assays of the invention may also include T cell immunogenicity assays (inhibitory or stimulatory) as well as MHC binding assays. In addition, immunological imaging methods capable of detecting cancers or endometriosis expressing MELK are also provided by the invention, including, but not limited to, radioscintigraphic imaging methods using labeled antibodies of the present invention. Such assays can find clinical use in the detection, monitoring, and prognosis of MELK expressing endometriosis or cancers, examples of which include, but are not limited to, breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC.

The present invention also provides an antibody that binds to the peptide of the invention. The antibody of the invention can be used in any form, such as monoclonal or polyclonal antibodies, and include antiserum obtained by immunizing an animal such as a rabbit with the peptide of the invention, all classes of polyclonal and monoclonal antibodies, human antibodies and humanized antibodies produced by genetic recombination.

A peptide of the invention used as an antigen to obtain an antibody may be derived from any animal species, but preferably is derived from a mammal such as a human, mouse, or rat, more preferably from a human. A human-derived peptide may be obtained from the nucleotide or amino acid sequences disclosed herein.

According to the present invention, the peptide to be used as an immunization antigen may be a complete protein or a partial peptide of the protein. A partial peptide may include, for example, the amino (N)-terminal or carboxy (C)-terminal fragment of a peptide of the present invention.

Herein, an antibody is defined as a protein that reacts with either the full length or a fragment of a MELK peptide. In a preferred embodiment, an antibody of the present invention can recognize fragment peptides of MELK having an amino acid sequence selected from among SEQ ID NOs: 35, 41, 44. Methods for synthesizing oligopeptide are well known in the arts. After the synthesis, peptides may be optionally purified prior to use as immunogen. In the present invention, the oligopeptide (e.g., 9- or 10mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, but preferably the compatibility with parental cells used for cell fusion is taken into account. In general, animals of Rodentia, Lagomorpha or Primates family may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for the immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies may include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, in which a non-human animal is immunized with an antigen for preparing hybridoma, human lymphocytes such as those infected by EB virus may be immunized with a peptide, peptide expressing cells or their lysates in vitro. Then, the immunized lymphocytes are fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the peptide of the present invention is coupled. The antibody of the present invention can be used not only for purification and detection of the peptide of the present invention, but also as a candidate for agonists and antagonists of the peptide of the present invention.

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the peptides of the invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239: 1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584; 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Exemplary chromatography, with the exception of affinity includes, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of a peptide of the invention, by exposing an antibody of the invention to a sample presumed to contain a peptide of the invention, and detecting or measuring the immune complex formed by the antibody and the peptide.

Because the method of detection or measurement of the peptide according to the invention can specifically detect or measure a peptide, the method can find use in a variety of experiments in which the peptide is used.

XII. VECTORS AND HOST CELLS

The present invention also provides a vector and host cell into which a nucleotide encoding the peptide of the present invention is introduced. A vector of the present invention can find use to keep a nucleotide, especially a DNA, of the present invention in host cell, to express the peptide of the present invention, or to administer the nucleotide of the present invention for gene therapy.

When *E. coli* is a host cell and the vector is amplified and produced in a large amount in *E. coli* (e.g., JM109, DH5 alpha, HB101 or XL1Blue), the vector should have "ori" to be amplified in *E. coli* and a marker gene for selecting transformed *E. coli* (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use.

For example, an expression vector to be expressed in *E. coli* should have the above characteristics to be amplified in *E. coli*. When *E. coli*, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the *E. coli* is the pelB signal sequence (Lei et al., J Bacteriol 169: 4379 (1987)). Means for introducing of the vectors into the target host cells include, for example, the calcium chloride method, and the electroporation method.

In addition to *E. coli*, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "*Pichia* Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells, such as CHO, COS or NIH3T3 cells, the vector should have a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

The following examples are presented to illustrate the present invention and to assist one of ordinary skill in making and using the same. The examples are not intended in any way to otherwise limit the scope of the invention.

EXAMPLES

Materials and Methods

Cell Lines

TISI, human leukocyte antigen (HLA)-A*2402 positive B-lymphoblastoid cell line, was purchased from the IHWG Cell and Gene Bank (Seattle, Wash.). COS7, MDA-MB-435S and T47D were purchased from ATCC. KLM-1 and KP-1N were purchased from RIKEN cell bank and JCRB cell bank, respectively.

Candidate Selection of Peptides Derived from MELK 9-mer and 10-mer peptides derived from MELK and that bind to HLA-A*2402 molecule were predicted using binding prediction software "BIMAS" (www-bimas.cit.nih.gov/molbio/hla_bind), which algorithms had been described by Parker K C et al. (J Immunol 1994, 152(1): 163-75) and Kuzushima K et al. (Blood 2001, 98(6): 1872-81). HIV peptide restricted for HLA-A*2402 (RYLRQQLLGI (SEQ ID NO: 48)) were used as a control. These peptides were synthesized by Biosynthesis Inc. (Lewisville, Tex.) according to the standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce cytotoxic T lymphocyte (CTL) responses against peptides presented on HLA. DCs were generated in vitro as described elsewhere (Nakahara S et al., Cancer Res 2003 Jul. 15, 63(14): 4112-8). Specifically, peripheral blood mononuclear cells (PBMCs) isolated from three healthy donors termed donors A, B and C (HLA-A*2402 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1,000 U/ml of granulocyte-macrophage colony-stimulating factor (GM-CSF) (R&D System) and 1,000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro-g/ml of each of the synthesized peptides in the presence of 3 micro-g/ml of beta2-microglobulin for 3 hrs at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X-irradiation (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. 3 days later, these cultures were supplemented with IL-2 (CHIRON) to a final concentration of 20 IU/ml. On days 7 and 14, the T cells were further stimulated with the autologous peptide-pulsed DCs. The DCs were prepared each time by the same way described above. CTLs were tested against peptide-pulsed A24LCL cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 Feb. 2(2): 216-23). A total of $5 \times 10^4$ CTLs were suspended in 25 ml of AIM-V/5% AS medium with 2 kinds of human B-lymphoblastoid cell lines, inactivated by MMC, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 micro-l/well of AIM-V Medium containing 5% AS. 50 micro-l/well of IL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed A24LCL ($1 \times 10^4$/well) and tumor cell lines ($5 \times 10^4$/well) were prepared as stimulator cells. Cultured cells in 48 wells, CTL lines and clones were used as responder cells. IFN-gamma ELISPOT assay and IFN-gamma ELISA assay were performed under manufacture procedure.

Plasmid Transfection

The cDNA encoding an open reading frame of target gene or HLA-A*2402 was amplified by PCR. The PCR-amplified products were cloned into pCAGGS vector. The plasmids were transfected into COST, which is the target genes and HLA-A24 negative cell line, using lipofectamine 2000 (Invitrogen) according to the manufacturer's recommended procedures. After 2 days from transfection, the transfected cells were harvested with versene (Invitrogen) and used as stimulator cells ($5 \times 10^4$ cells/well) for CTL activity assay.

Inhibition Assay

To confirm the HLA-class I-restricted CTL activity, stimulator cells were incubated with 10 micro-g/ml of anti-HLA class I monoclonal antibody W6/32 (BioLegend) or normal mouse IgG (Santa Cruz Biotechnology) for 30 min at 4 degrees C. The treated cells were used as the stimulator to examine the CTL activity.

Results

Prediction of HLA-A24 Binding Peptides Derived from MELK

Tables 1A and 1B show the HLA-A24 binding 9mer and 10mer peptides derived from MELK in the order of high binding affinity. A total of 34 peptides with potential HLA-A24 binding ability were selected and examined to determine the epitope peptides.

TABLE 1A

HLA-A24 binding 9mer peptides derived from MELK

| SEQ ID NO. | Start Position | Amino acid sequence | Binding Score |
|---|---|---|---|
| 1 | 199 | LYVLMCGFL | 300 |
| 2 | 96 | DYIISQDRL | 300 |
| 3 | 560 | HYNVTTTRL | 300 |
| 4 | 373 | DYDWCEDDL | 200 |
| 5 | 9 | KYYELHETI | 144 |
| 6 | 87 | EYCPGGELF | 120 |
| 7 | 637 | VYKRLVEDI | 60 |
| 8 | 610 | QFELEVCQL | 30 |
| 9 | 588 | DFVQKGYTL | 30 |
| 10 | 526 | VFGSLERGL | 24 |
| 11 | 567 | RLVNPDQLL | 14.4 |
| 12 | 603 | DFGKVTMQF | 14 |
| 13 | 522 | KGAKVFGSL | 13.4 |
| 14 | 326 | RGKPVRLRL | 13.4 |
| 15 | 450 | KNQHKREIL | 12 |
| 16 | 230 | KWLSPSSIL | 12 |
| 17 | 395 | KYWTESNGV | 12 |
| 18 | 502 | RCRSVELDL | 11.2 |
| 19 | 145 | KLKLIDFGL | 11.2 |
| 20 | 574 | LLNEIMSIL | 10.1 |
| 21 | 78 | TANKIFMVL | 10.1 |
| 22 | 225 | KYDVPKWLS | 10 |

TABLE 1B

HLA-A24 binding 10mer peptides derived from MELK

| SEQ ID NO. | Start Position | Amino acid sequence | Binding Score |
|---|---|---|---|
| 23 | 637 | VYKRLVEDIL | 280 |
| 24 | 309 | QYDHLTATYL | 200 |
| 25 | 142 | EYHKLKLIDF | 100 |
| 26 | 139 | LFDEYHKLKL | 26.4 |
| 27 | 532 | RGLDKVITVL | 20.2 |
| 28 | 230 | KWLSPSSILL | 12 |
| 29 | 55 | KTEIEALKNL | 12 |
| 30 | 295 | RNNRQTMEDL | 12 |
| 31 | 223 | RGKYDVPKWL | 11.2 |
| 32 | 632 | KGDAWVYKRL | 11.2 |
| 33 | 266 | DYNYPVEWQS | 10.5 |
| 34 | 463 | RYTTPSKARN | 10 |

Start position indicates the number of amino acid residue from the N-terminus of MELK.
Binding score is derived from "BIMAS".

CTL Induction with the Predicted Peptides from MELK Restricted with HLA-A*2402

CTLs from PBMCs of donor A for those peptides derived from MELK were generated according to the protocols as described in "Materials and Methods". Peptide specific CTL activity was determined by IFN-gamma ELISPOT assay (FIG. 1). The following well numbers demonstrated potent IFN-gamma production as compared to the control wells: well number #2 stimulated with MELK-A24-9-87 (SEQ ID NO: 6) (a), #1 and #3 stimulated with MELK-A24-10-637 (SEQ ID NO: 23) (b), #8 stimulated with MELK-A24-9-199 (SEQ ID NO: 1) (d) and #4 stimulated with MELK-A24-9-78 (SEQ ID NO: 21) (e) demonstrated potent IFN-gamma production as compared to the control wells. On the other hand, no potent IFN-gamma production could be detected by stimulation with other peptides shown in Table 1, despite those peptides had possible binding activity with HLA-A*2402. For example, typical negative data of CTL response stimulated with MELK-A24-9-96 (SEQ ID NO: 2) was shown in FIG. 1 (c). As a result, it indicated that four peptides derived from MELK were screened as the peptides that could induce potent CTLs.

Establishment of CTL Lines and Clones Against MELK Specific Peptides

Figure 2:
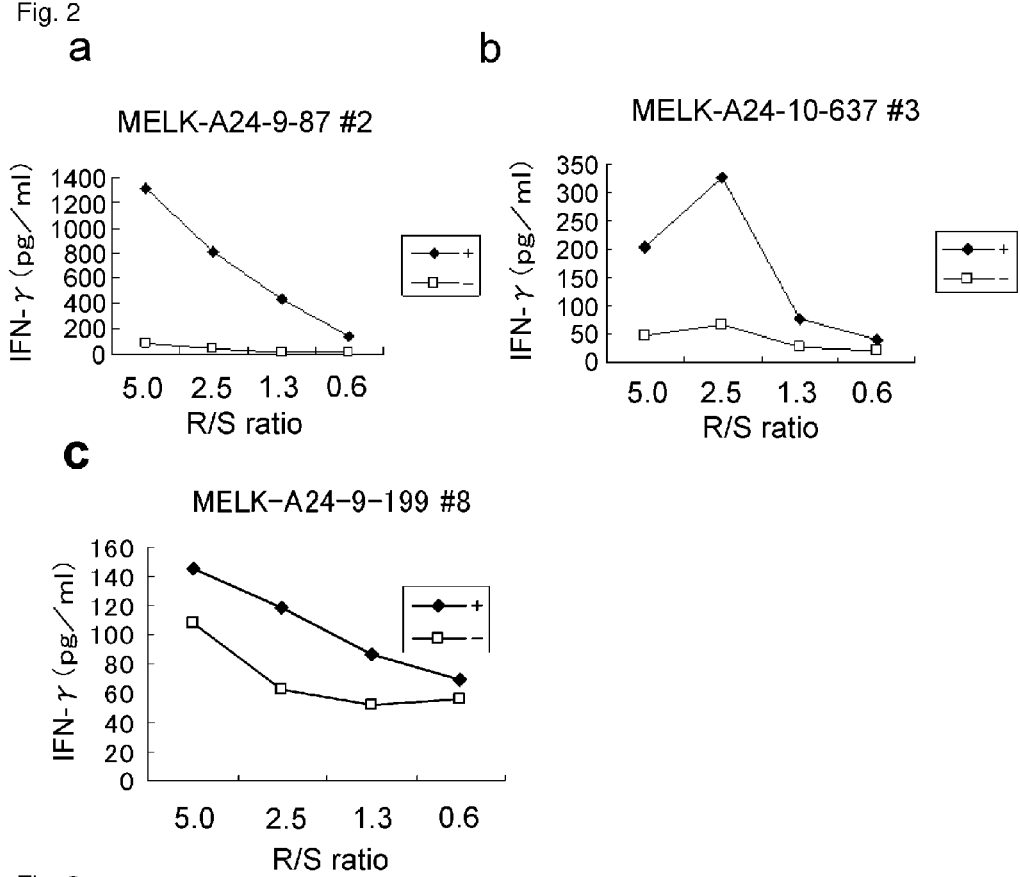
FIG. 2 depicts the line graphs showing the result of the establishment of CTL lines. The potent IFN-gamma production was detected from the CTL lines stimulated with MELK-A24-9-87 (SEQ ID NO: 6) (a), MELK-A24-10-637 (SEQ ID NO: 23) (b) and MELK-A24-9-199 (SEQ ID NO: 1) (c) by IFN-gamma ELISA assay. In the figures, "black lozenge" indicates the IFN-gamma production against target cells pulsed with cognate peptides and "white square" indicates the IFN-gamma production against target cells not pulsed with any peptides.
Figure 3:
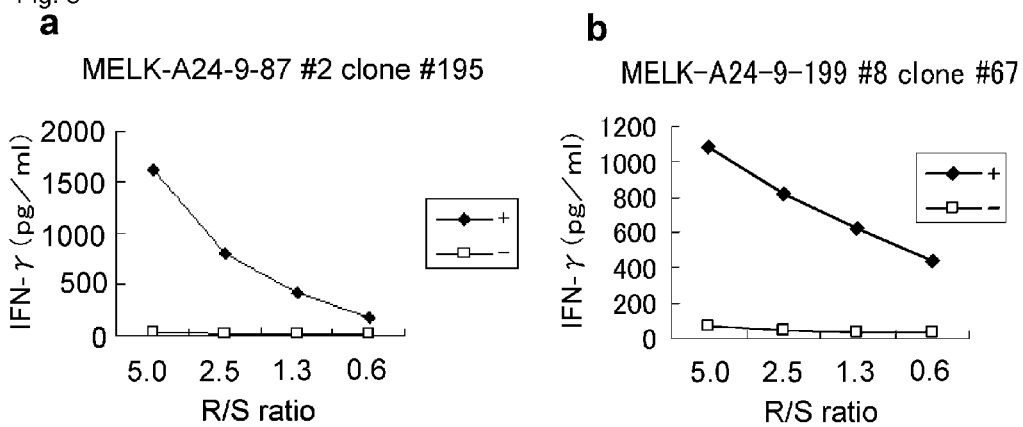
FIG. 3 depicts the line graph showing the result of the establishment of the CTL clone. The potent IFN-gamma production was detected from the CTL clone stimulate with MELK-A24-9-87 (SEQ ID NO: 6) (a) and MELK-A24-9-199 (SEQ ID NO: 1) (b) by IFN-gamma ELISA assay. In the figure, "black lozenge" indicates the IFN-gamma production against target cells pulsed with MELK-A24-9-87 (SEQ ID NO: 6) and "white square" indicates the IFN-gamma production against target cells not pulsed with any peptides.

The cells that showed peptide specific CTL activity detected by IFN-gamma ELISPOT assay in the well number #2 stimulated with MELK-A24-9-87 (SEQ ID NO: 6) and #3 stimulated with MELK-A24-10-637 (SEQ ID NO: 23) were expanded and established CTL lines. The CTL activity of those CTL lines was determined by IFN-gamma ELISA assay (FIG. 2). All CTL lines demonstrated potent IFN-gamma production against the target cells pulsed with MELK-A24-9-87 (SEQ ID NO: 6) (a) MELK-A24-10-637 (SEQ ID NO: 23) (b) and MELK-A24-9-199 (SEQ ID NO: 1) (c) as compared to the target cells without peptide pulse. Furthermore, the CTL lines were diluted and cultured to establish CTL clones as described in "Materials and Methods". The IFN-gamma production from the CTL clones against the target cells pulsed with cognate peptides was determined by IFN-gamma ELISA assay. Potent IFN-gamma production was determined from the CTL clone stimulated with MELK-A24-9-87 (SEQ ID NO: 6) and MELK-A24-9-199 (SEQ ID NO: 1) in FIG. 3.

Specific CTL Activity Against Target Cells Expressing MELK and HLA-A*2402

Figure 4:
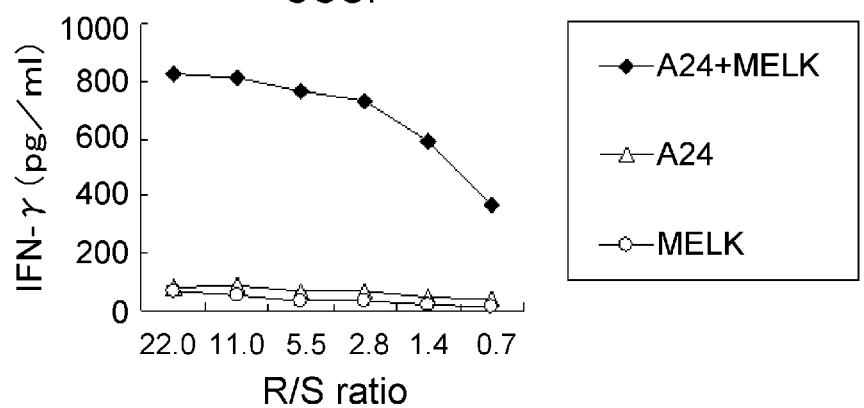
FIG. 4 depicts the line graph showing the specific CTL activity against the target cells that exogenously express MELK and HLA-A*2402. COS7 cells transfected with HLA-A*2402 or the full length of MELK gene were prepared as controls. The CTL clone established with MELK-A24-9-87 (SEQ ID NO: 6) showed specific CTL activity against COS7 cells transfected with both MELK and HLA-A*2402 (black lozenge). On the other hand, no significant specific CTL activity was detected against target cells expressing either HLA-A*2402 (white triangle) or MELK (white circle).

The established CTL clone raised against MELK-A24-9-87 (SEQ ID NO: 6) was examined for their ability to recognize target cells that express MELK and HLA-A*2402. Specific CTL activity against COS7 cells which transfected with both the full length of MELK and HLA-A*2402 (a specific model for the target cells that express MELK and HLA- A*2402) was tested using the CTL clone stimulated with MELK-A24-9-87 (SEQ ID NO: 6). COS7 cells transfected with either full length of MELK or HLA-A*2402 were prepared as controls. In FIG. 4, the CTL clone stimulated with MELK-A24-9-87 (SEQ ID NO: 6) showed potent CTL activity against COS7 cells expressing both MELK and HLA-A*2402. On the other hand, no significant specific CTL activity was detected against the controls. Thus, these data clearly demonstrated that peptides of MELK-A24-9-87 (SEQ ID NO: 6) were endogenously processed and presented on the target cells with HLA-A*2402 molecule and were recognized by the CTLs.

Prediction of HLA-A24 Binding MELK-A24-9-87 Modified Peptides

Subsequently, the present inventors investigated the modified peptides substituting one amino acid residue from MELK-A24-9-87 (SEQ ID NO: 6) that have the potential ability to induce MELK-A24-9-87 specific CTLs more efficiently than wild type MELK-A24-9-87 (MELK-A24-9-87_WT) (SEQ ID NO: 6). Table 2 shows candidate peptides that are modified the sequence of MELK-A24-9-87_WT (SEQ ID NO: 6) in the order of high binding affinity. A total of 11 peptides that were predicted to have higher binding ability compared to MELK-A24-9-87_WT (SEQ ID NO: 6) were selected and examined the immunogenicity.

TABLE 2

Modified peptides from MELK-A24-9-87

| SEQ ID NO. | Peptide name | Amino acid sequence | Binding score |
|---|---|---|---|
| 35 | MELK-A24-9-87_1K | KYCPGGELF | 240 |
| 36 | MELK-A24-9-87_1R | RYCPGGELF | 240 |
| 37 | MELK-A24-9-87_9L | EYCPGGELL | 240 |
| 38 | MELK-A24-9-87_3E | EYEPGGELF | 180 |
| 39 | MELK-A24-9-87_3I | EYIPGGELF | 180 |
| 40 | MELK-A24-9-87_3L | EYLPGGELF | 180 |
| 41 | MELK-A24-9-87_3M | EYMPGGELF | 180 |
| 42 | MELK-A24-9-87_3N | EYNPGGELF | 180 |
| 43 | MELK-A24-9-87_3P | EYPPGGELF | 180 |
| 44 | MELK-A24-9-87_7N | EYCPGGNLF | 144 |
| 45 | MELK-A24-9-87_7Q | EYCPGGQLF | 144 |
| 6 | MELK-A24-9-87_WT | EYCPGGELF | 120 |

Binding score is derived from "BIMAS".

CTL Induction with the Modified Peptides from MELK-A24-9-87

Figure 5A:
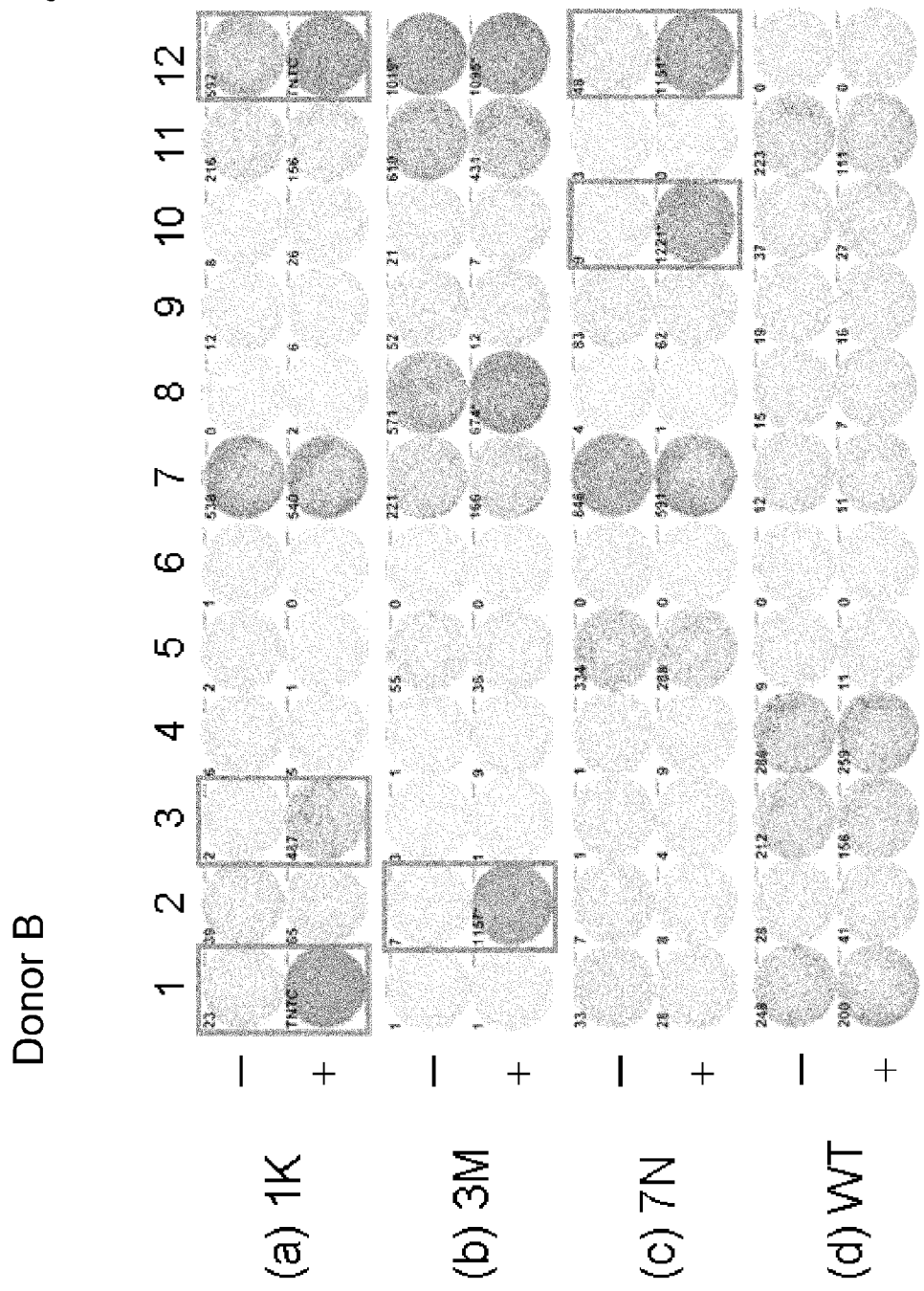
FIG. 5A depicts the photographs showing the result of IFN-gamma ELISPOT assays on CTLs of donor B induced with modified peptides from MELK-A24-9-87_WT (SEQ ID NO: 6). The CTLs stimulated with MELK-A24-9-87_1K (SEQ ID NO: 35) (a), MELK-A24-9-87_3M (SEQ ID NO: 41) (b) and MELK-A24-9-87_7N (SEQ ID NO: 44) (c) showed potential IFN-gamma productive ability as indicated with the square. On the other hand, the peptide specific IFN-gamma production was not detected from the CTL stimulated with MELK-A24-9-87_WT (SEQ ID NO: 6) (d). In the figures, "+" indicates the IFN-gamma production against the target cells pulsed with cognate peptides, and "−" indicates the IFN-gamma production against target cells not pulsed with any peptides.

CTLs reactive for modified peptides in Table 2 were generated according to the protocols as described in "Materials and Methods". Peptide specific CTL activity was determined by IFN-gamma ELISPOT assay. FIG. 5A shows the results of IFN-gamma ELISPOT assay on CTLs induced from PBMCs of donor B. The following well numbers demonstrated potent IFN-gamma production as compared to the control wells: well number #1, #3 and #12 stimulated with MELK-A24-9-87_1K (SEQ ID NO: 35) (a), #2 with MELK-A24-9-87_3M (SEQ ID NO: 41) (b) and #10 and #12 with MELK-A24-9-87_7N (SEQ ID NO: 44) (c). On the other hand, no specific IFN-gamma production was detected from the PBMCs stimulated with MELK-A24-9-87_WT (SEQ ID NO: 6) (d).

The PBMCs of another donor C were also stimulated with modified peptides in Table 2. FIG. 5B shows that the well number #14 stimulated with MELK-A24-9-87_7N (SEQ ID NO: 44) demonstrated potent IFN-gamma production compared with the controls (a). On the other hand, no specific IFN-gamma production was detected from the CTLs stimulated with MELK-A24-9-87_WT (SEQ ID NO: 6) (b) as well as PBMCs of donor B.

These results indicated that MELK-A24-9-87_1K (SEQ ID NO: 35), MELK-A24-9-87_3M (SEQ ID NO: 41) and MELK-A24-9-87_7N (SEQ ID NO: 44) have superior immunogenicity compared to MELK-A24-9-87_WT (SEQ ID NO: 6).

Establishment of CTL Lines and Clones by Stimulation with MELK Modified Peptides The cells that showed peptide specific CTL activity detected by IFN-gamma ELISPOT assay in the well number #1 stimulated with MELK-A24-9-87_1K (SEQ ID NO: 35), #2 with MELK-A24-9-87_3M (SEQ ID NO: 41) and #12 with MELK-A24-9-87_7N (SEQ ID NO: 44) from donor B and #14 stimulated with MELK-A24-9-87_7N (SEQ ID NO: 44) from donor C were expanded to establish CTL lines. The cells in the well number #4 stimulated with MELK-A24-9-87_WT (SEQ ID NO: 6) that showed minor IFN-gamma production were also expanded.

Figure 6:
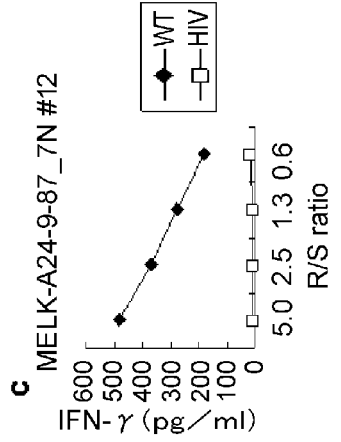
FIGS. 6a-c depict the line graphs showing the result of the establishment of CTL lines induced from PBMCs of donor B. The potent IFN-gamma production was detected from the CTL lines stimulated with MELK-A24-9-87_1K (SEQ ID NO: 35) (a), MELK-A24-9-87_3M (SEQ ID NO: 41) (b) and MELK-A24-9-87_7N (SEQ ID NO: 44) (c) by IFN-gamma ELISA assay. In the figures, "black lozenge" indicates the IFN-gamma production against target cells pulsed with MELK-A24-9-87_WT (SEQ ID NO: 6) and "white square" indicates the IFN-gamma production against target cells pulsed with the irrelevant HIV peptide.
FIGS. 6d-e depict the line graphs showing the result of the establishment of CTL lines induced from PBMCs of donor C. The IFN-gamma production was detected from the CTL lines stimulated with MELK-A24-9-87_7N (SEQ ID NO: 44) (d) by IFN-gamma ELISA assay. The CTL line was not established from PBMCs stimulated with MELK-A24-9-87_WT (SEQ ID NO: 6) (e). In the figures, "black lozenge" indicates the IFN-gamma production against target cells pulsed with MELK-A24-9-87_WT (SEQ ID NO: 6) and "white square" indicates the IFN-gamma production against target cells pulsed with the irrelevant HIV peptide.
Figure 6:
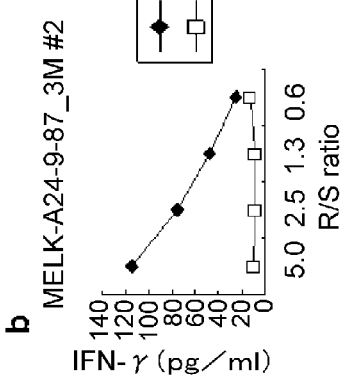
Figure 6:
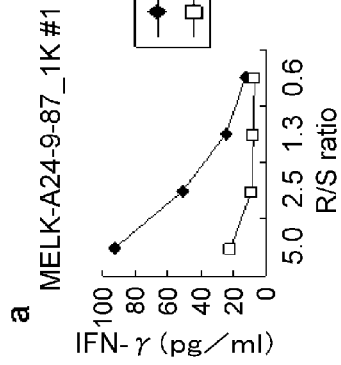
Figure 6:
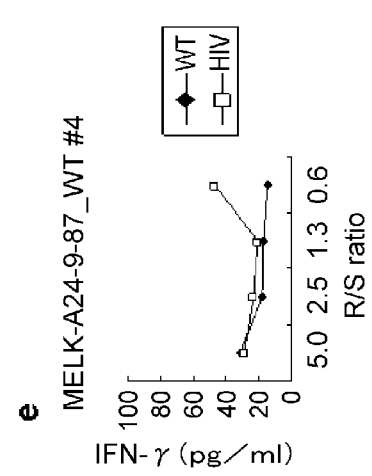
Figure 6:
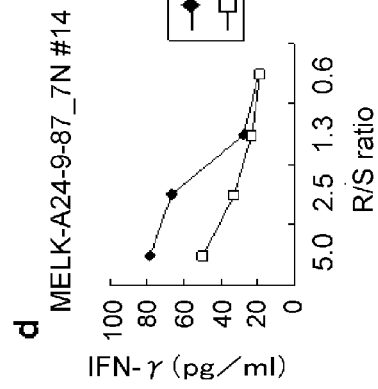

The CTL activity of those CTL lines was determined by IFN-gamma ELISA assay. In FIG. 6, the CTL lines from donor B stimulated with MELK-A24-9-87_1K (SEQ ID NO: 35) (a), MELK-A24-9-87_3M (SEQ ID NO: 41) (b) and MELK-A24-9-87_7N (SEQ ID NO: 44) (c) showed potent IFN-gamma production against the target cells pulsed with MELK-A24-9-87_WT (SEQ ID NO: 6) compared to the target cells pulsed with the irrelevant HIV peptide. The CTL line from donor C stimulated with MELK-A24-9-87_7N (SEQ ID NO: 44) also showed MELK-A24-9-87_WT (SEQ ID NO: 6) peptide specific IFN-gamma production (d), whereas the expanded cells stimulated with MELK-A24-9-87_WT (SEQ ID NO: 6) showed no IFN-gamma production against the target cells pulsed with MELK-A24-9-87_WT (SEQ ID NO: 6) (e).

Figure 7:
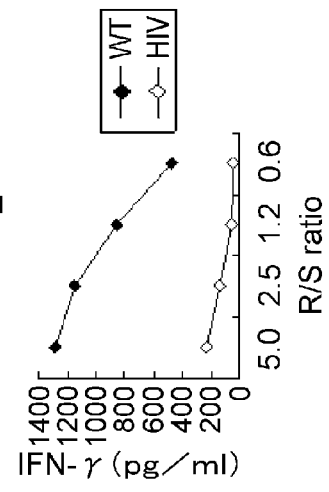
FIGS. 7a-c depict the line graphs showing the result of the establishment of CTL clones induced from PBMCs of donor B. The potent IFN-gamma production was detected from the CTL clones stimulated with MELK-A24-9-87_1K (SEQ ID NO: 35) (a), MELK-A24-9-87_3M (SEQ ID NO: 41) (b) and MELK-A24-9-87_7N (SEQ ID NO: 44) (c) by IFN-gamma ELISA assay. In the figure, "black lozenge" indicates the IFN-gamma production against target cells pulsed with MELK-A24-9-87_WT (SEQ ID NO: 6) and "white square" indicates the IFN-gamma production against target cells pulsed with the irrelevant HIV peptides.
FIG. 7d depicts the line graph showing the result of the establishment of the CTL clone induced from PBMCs of donor C. The potent IFN-gamma production was detected from the CTL clone stimulated with MELK-A24-9-87_7N (SEQ ID NO: 44) by IFN-gamma ELISA assay. In the figure, "black lozenge" indicates the IFN-gamma production against target cells pulsed with MELK-A24-9-87_WT (SEQ ID NO: 6) and "white square" indicates the IFN-gamma production against target cells pulsed with the irrelevant HIV peptides.
Figure 7:
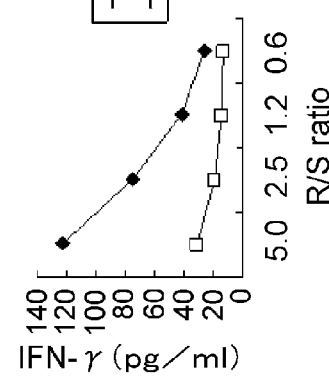
Figure 7:
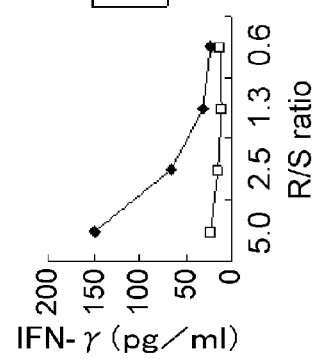
Figure 7:
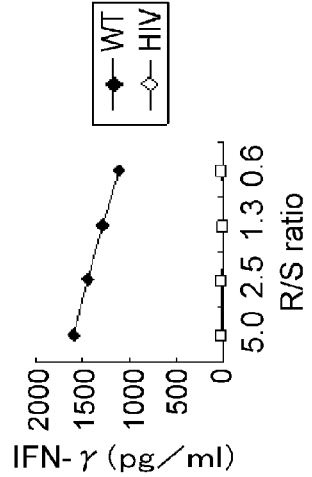

Subsequently, CTL clones were established by limiting dilution as described in "Materials and Methods", and CTL activity of those CTL clones was determined by IFN-gamma ELISA assay. The potent IFN-gamma productions were detected from CTL clones stimulated with MELK-A24-9-87_1K (SEQ ID NO: 35), MELK-A24-9-87_3M (SEQ ID NO: 41) and MELK-A24-9-87_7N (SEQ ID NO: 44) from donor B (FIGS. 7a-c) and MELK-A24-9-87_7N (SEQ ID NO: 44) from donor C (FIG. 7d) against the target cells pulsed with MELK-A24-9-87_WT (SEQ ID NO: 6) compared to the target cells pulsed with the irrelevant HIV peptide.

Taken together with the results of CTL induction of these two donors, it demonstrated that the MELK-A24-9-87_1K (SEQ ID NO: 35), MELK-A24-9-87_3M (SEQ ID NO: 41) and MELK-A24-9-87_7N (SEQ ID NO: 44) have superior immunogenicity to induce potent MELK-A24-9-87-reactive CTLs compared to MELK-A24-9-87_WT (SEQ ID NO: 6).

Specific CTL Activity Against Target Cells Expressing MELK and HLA-A*2402

Figure 8:
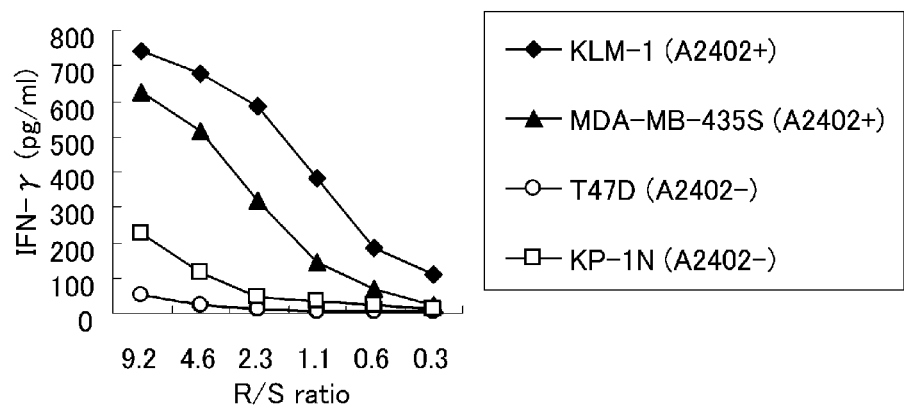
FIG. 8 depicts the line graphs showing the specific CTL activity against the target cells that endogenously express MELK and HLA-A*2402. (a) The CTL line established with MELK-A24-9-87_7N (SEQ ID NO: 44) showed specific CTL activity against tumor cell lines expressed both MELK and HLA-A*2402 (black lozenge; KLM-1, black triangle; MDA-MB-4355) compared with other cell lines which expressed MELK but not expressed HLA-A*2402 (white circle; T47D, white square; KP-1N). (b) Inhibition of the CTL response by treatment of anti-HLA class I mAb was shown. The CTL clone established with MELK-A24-9-87_7N (SEQ ID NO: 44) showed specific CTL activity against KLM-1 (black lozenge) compared with KP-1N (white square). The IFN-gamma production against KLM-1 (black lozenge) was inhibited by treatment of anti-HLA class I mAb (white lozenge) compared with the treatment of normal mouse IgG as a control (hyphen).
Figure 8:
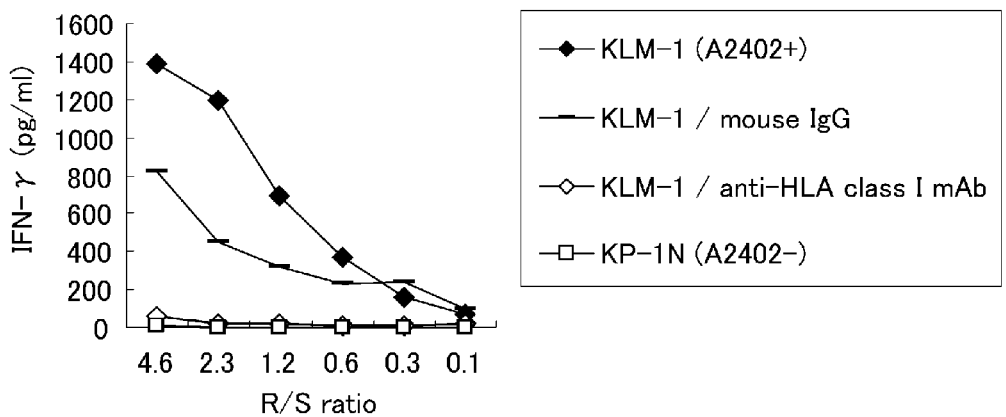
Figure 9:
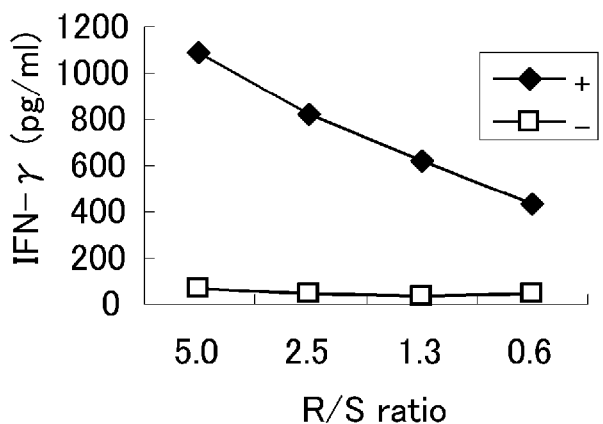
FIG. 9 depicts the line graphs showing the result of the reactivity of MELK-A24-9-199 (SEQ ID NO: 1) specific CTL clone.
Figure 9:
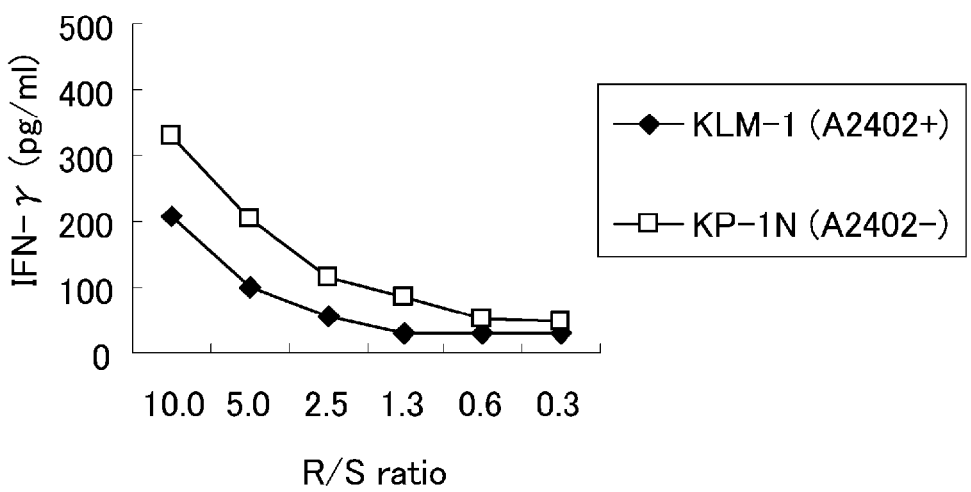

The established CTL lines and clones were examined for their ability to recognize target cells that express MELK and HLA-A*2402. In FIG. 8a, the CTL line stimulated with MELK-A24-9-87_7N (SEQ ID NO: 44) showed potent CTL activity against tumor cell lines MDA-MB-4355 (MELK+, A24+) and KLM-1 (MELK+, A24+) without showing CTL activity against T47D (MELK+, A24−) and KP-1N (MELK+, A24−). To confirm that this CTL activity was caused in an HLA-class I-restricted manner, the inhibition assay was performed using the anti-HLA-class I monoclonal antibody to block the antigen-specific responses of the CTLs. In FIG. 8b, the IFN-gamma production of CTLs against KLM-1 (MELK+, A24+) was completely inhibited by anti-HLA-class I monoclonal antibody compared to normal mouse IgG. These results clearly demonstrated that the CTLs induced with MELK-A24-9-87_7N (SEQ ID NO: 44) could recognize the naturally expressed MELK epitope peptide on the target cells with HLA-A*2402 molecule in an HLA-class I-restricted manner. As typical negative data, FIG. 9 shows the IFN-gamma production of MELK-A24-9-199 (SEQ ID NO: 1) specific CTL clone against the target cells pulsed with MELK-A24-9-199 (SEQ ID NO: 1) (a) and the tumor cell lines KLM-1 (MELK+, A24+) and KP-1N (MELK+, A24−) (b). Though MELK-A24-9-199 (SEQ ID NO: 1) specific CTL clone had the ability to recognize the peptide-pulsed target cells, it showed no IFN-gamma production against tumor cell lines KLM-1 (MELK+, A24+). These results suggested that MELK-A24-9-199 (SEQ ID NO: 1) is not naturally presented on the tumor cells expressing MELK.

Homology Analysis of Antigen Peptides

The CTLs stimulated with MELK-A24-9-87 (SEQ ID NO: 6), MELK-A24-10-637 (SEQ ID NO: 23), MELK-A24-9-87_1K (SEQ ID NO: 35), MELK-A24-9-87_3M (SEQ ID NO: 41) and MELK-A24-9-87_7N (SEQ ID NO: 44) showed significant and specific CTL activity. This result may be due to the fact that the sequences of MELK-A24-9-87 (SEQ ID NO: 6), MELK-A24-10-637 (SEQ ID NO: 23), MELK-A24-9-87_1K (SEQ ID NO: 35), MELK-A24-9-87_3M (SEQ ID NO: 41) and MELK-A24-9-87_7N (SEQ ID NO: 44) are homologous to peptides derived from other molecules that are known to sensitize the human immune system. To exclude this possibility, homology analyses were performed for these peptide sequences using as queries the BLAST algorithm (www.ncbi.nlm.nih.gov/blast/blast.cgi) which revealed no sequence with significant homology. The results of homology analyses indicate that the sequences of MELK-A24-9-87 (SEQ ID NO: 6), MELK-A24-10-637 (SEQ ID NO: 23), MELK-A24-9-87_1K (SEQ ID NO: 35), MELK-A24-9-87_3M (SEQ ID NO: 41) and MELK-A24-9-87_7N (SEQ ID NO: 44) are unique and thus, there is little possibility, to our best knowledge, that these molecules raise unintended immunologic response to some unrelated molecule.

In conclusion, novel epitope peptides that had modified sequence of MELK-A24-9-87 (SEQ ID NO: 6) derived from MELK were identified. The results presented here demonstrate that MELK-A24-9-87_7N (SEQ ID NO: 44), the modified peptides from MELK-A24-9-87 (SEQ ID NO: 6), efficiently induce CTLs that recognize the MELK expressing target cells and show potent CTL activity compared to MELK-A24-9-87 (SEQ ID NO: 6).

INDUSTRIAL APPLICABILITY

The present invention describes new TAAs, particularly those derived from modified MELK peptide that induce potent and specific anti-tumor immune responses and have applicability to a wide array of diseases, including cancer. Such TAAs are useful as peptide vaccines against diseases associated with MELK overexpression, e.g., endometriosis or cancer, more particularly, breast cancer, bladder cancer, cervical cancer, cholangiocellular carcinoma, CML, colorectal cancer, esophagus cancer, gastric cancer, liver cancer, NSCLC, lymphoma, osteosarcoma, ovarian cancer, pancreatic cancer, prostate cancer, renal carcinoma and SCLC.

While the invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention, the metes and bounds of which are defined by the appended claims.

The invention claimed is:

1. An isolated peptide that can bind to an HLA antigen and has cytotoxic T lymphocyte (CTL) inducibility, wherein the peptide consists of an amino acid sequence having one or more amino acid substitutions in the amino acid sequence of SEQ ID NO: 6 selected from the group consisting of (a) to (c): (a) the N-terminal amino acid, (b) the third amino acid from the N-terminus and (c) the third amino acid from the C-terminus.

2. The isolated peptide of claim 1, wherein the HLA antigen is HLA-A24.

3. The isolated peptide of claim 1, wherein the peptide has one or more amino acid substitutions selected from the group consisting of (i) to (iii):
   (i) amino acid substitution from E to K or R at the N-terminal amino acid in the amino acid sequence of SEQ ID NO: 6,
   (ii) amino acid substitution from C to E, I, L, M, N or P at the third amino acid from the N-terminus in the amino acid sequence of SEQ ID NO: 6, and
   (iii) amino acid substitution from E to N or Q at the third amino acid from the C-terminus in the amino acid sequence of SEQ ID NO: 6.

4. The isolated peptide of claim 3, wherein the number of the amino acid substitutions is one.

5. The isolated peptide of claim 3, wherein the number of the amino acid substitutions is two or three.

6. The isolated peptide of claim 4, wherein the peptide consists of an amino acid sequence selected from the group consisting of SEQ ID NOs: 44, 35, and 41.

7. An isolated peptide that can bind to an HLA antigen and has cytotoxic T lymphocyte (CTL) inducibility, wherein the peptide consists of an amino acid sequence selected from the group consisting of SEQ ID NOs: 44, 35, and 41, in which 1 or 2 amino acid(s) are inserted, substituted, deleted or added, wherein said peptide is not SEQ ID NO: 6.

8. The isolated peptide of claim 7, wherein the peptide has one or both of the following characteristics:
   (a) the second amino acid from the N-terminus of the amino acid sequence of SEQ ID NO: 44, 35 or 41 is substituted with an amino acid selected from the group consisting of phenylalanine, methionine and tryptophan; and
   (b) the C-terminal amino acid of the amino acid sequence of SEQ ID NO: 44, 35 or 41 is substituted with an amino acid selected from the group consisting of, leucine, isoleucine, tryptophan and methionine.

9. A composition for inducing a CTL, wherein the composition comprises one or more peptide(s) of claim 1 or 7.

10. A composition comprising one or more peptide(s) of claim 1 or 7.

11. The composition of claim 10, wherein said composition is formulated for the administration to a subject whose HLA antigen is HLA-A24.

12. A method for inducing an antigen-presenting cell (APC) with CTL inducibility, wherein the method comprises the step of
   contacting an APC with the peptide of claim 1 or 7 in vitro, ex vivo or in vivo.

13. A method for inducing a CTL by any of the methods comprising at least one of the following steps:
   (a) co-culturing CD8-positive T cells with APCs which present on its surface a complex of an HLA antigen and the peptide of claim 1 or 7 and
   (b) co-culturing CD8-positive T cells with exosomes which present on its surface a complex of an HLA antigen and the peptide of claim 1 or 7.

14. A method of inducing immune response against cancer or endometriosis in a subject, wherein the method comprises administering to the subject a composition comprising a peptide of claim 1 or 7.

* * * * *